United States Patent
Nakao et al.

(10) Patent No.: US 11,046,770 B2
(45) Date of Patent: Jun. 29, 2021

(54) ANTI-HUMAN BDCA-2 ANTIBODY

(71) Applicant: Astellas Pharma Inc., Tokyo (JP)

(72) Inventors: Shinsuke Nakao, Tokyo (JP); Masayuki Ito, Tokyo (JP); Yoshiyuki Tenda, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 121 days.

(21) Appl. No.: 16/384,811

(22) Filed: Apr. 15, 2019

(65) Prior Publication Data
US 2019/0248904 A1 Aug. 15, 2019

Related U.S. Application Data

(62) Division of application No. 15/107,660, filed as application No. PCT/JP2014/083862 on Dec. 22, 2014, now Pat. No. 10,294,301.

(30) Foreign Application Priority Data

Dec. 24, 2013 (JP) ................................. 2013-265304

(51) Int. Cl.
*C07K 16/28* (2006.01)

(52) U.S. Cl.
CPC ...... *C07K 16/2851* (2013.01); *C07K 2317/21* (2013.01); *C07K 2317/24* (2013.01); *C07K 2317/51* (2013.01); *C07K 2317/52* (2013.01); *C07K 2317/56* (2013.01); *C07K 2317/565* (2013.01); *C07K 2317/76* (2013.01); *C07K 2317/92* (2013.01); *C12N 2510/00* (2013.01)

(58) Field of Classification Search
None
See application file for complete search history.

(56) References Cited

U.S. PATENT DOCUMENTS

2013/0315820 A1 11/2013 Fournier et al.

FOREIGN PATENT DOCUMENTS

| WO | WO 01/36487 A2 | 5/2001 |
| WO | WO 2014/093396 A1 | 6/2014 |
| WO | WO 2015/095143 A1 | 6/2015 |

OTHER PUBLICATIONS

International Search Report dated Mar. 24, 2015, in PCT/JP2014/083862, with English translation.
Cao et al., "BDCA2/FcεRIγ Complex Signals through a Novel BCR-Like Pathway in Human Plasmacytoid Dendritic Cells," PLoS Biology, Oct. 2007, 5(10):e248:2190-2200.
Dzionek et al., "BDCA-2, a Novel Plasmacytoid Dendritic Cell-specific Type II C-type Lectin, Mediates Antigen Capture and Is a Potent Inhibitor of Interferon α/β Induction," J. Exp. Med., Dec. 17, 2001, 194(12):1823-1834.
Jähn et al., "BDCA-2 signaling inhibits TLR-9-agonist-induced plasmacytoid dendritic cell activation and antigen presentation," Cellular Immunology, 2010, 265:15-22.
Office Action dated Jul. 4, 2018, in Chinese Application No. 2014800701796, with English translation.
Office Action dated Sep. 25, 2018, in Japanese Application No. 2015-554867, with English translation.
Office Action dated Apr. 2, 2019, in Japanese Application No. 2015-554867, with English translation.
Pellerin et al., "Anti-BDCA2 monoclonal antibody inhibits plasmacytoid dendritic cell activation through Fc-dependent and Fc-independent mechanisms," EMBO Molecular Medicine, Apr. 1, 2015, 7(4):464-476.
Röck et al., "CD303 (BDCA-2) signals in plasmacytoid dendritic cells via a BCR-like signalosome involving Syk, Slp65 and PLCγ2," Eur. J. Immunol., 2007, 37(12):3564-3575.
Supplementary European Search Report dated Aug. 11, 2017, in EP 14873919.6.
Office Action dated Aug. 13, 2019, in corresponding Mexican patent application No. MX/a/2016/008520, with English translation.
Office Action dated Apr. 1, 2019, in corresponding Chinese application No. 20180070179.6, with English translation.
Office Action dated Feb. 8, 2021 in EP 14873919.6.

*Primary Examiner* — Amy E Juedes
(74) *Attorney, Agent, or Firm* — Foley & Lardner LLP

(57) ABSTRACT

[Problem] Provided is an anti-human BDCA-2 antibody for preventing or treating an autoimmune disease by binding to a human BDCA-2 to control the function of a plasmacytoid dendritic cell through human BDCA-2.

[Means for Solution] The present inventors have investigated anti-human BDCA-2 antibodies, and as a result, they have provided an anti-human BDCA-2 antibody comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4, a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8, and a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

6 Claims, No Drawings

Specification includes a Sequence Listing.

ANTI-HUMAN BDCA-2 ANTIBODY

CROSS-REFERENCE TO RELATED APPLICATIONS

This application is a Divisional of U.S. application Ser. No. 15/107,660, filed on Jun. 23, 2016, which is a National Stage application of PCT/JP2014/083862, filed Dec. 22, 2014, which claims priority from Japanese application 2013-265304, filed Dec. 24, 2013.

TECHNICAL FIELD

The present invention relates to a novel anti-human BDCA-2 antibody.

BACKGROUND ART

Blood Dendritic Cell Antigen 2 (BDCA-2) is a single-pass transmembrane type of membrane protein. BDCA-2 is known to be expressed restrictively in human plasmacytoid dendritic cells (pDCs). BDCA-2 plays a role in controlling functions of pDCs by transmitting signal into pDCs (Int. Immunol., Vol. 25, p. 271-277, 2013).

BDCA-2 is known to function with respect to activated immune responses in an inhibitory manner (Non-Patent Document 1). The details of this mechanism is still unclear in many parts, but as described later, it has been reported that pDCs in the activated state can be inhibited by crosslinking BDCA-2 molecules using an antibody against BDCA-2 (Patent Document 1, and Non-Patent Documents 1 to 4).

It is known that pDCs, which are the cells specifically expressing BDCA-2, are abnormally activated in peripheral blood or disorder sites and produce interferon (IFN) α in a large amount, in autoimmune diseases such as systemic lupus erythematosus, scleroderma, polymyositis and dermatomyositis, psoriasis, Sjoegren's syndrome, rheumatoid arthritis, Grave's disease, and Hashimoto's disease. It has been found that pDCs are deeply involved in the pathology of autoimmune diseases (Arthritis Rheum., Vol. 65, p. 853-863, 2013).

It has been reported that in systemic lupus erythematosus, which is a type of autoimmune disease, there is a positive correlation to the severity and the concentration of IFN α in the blood of patients (Lupus, Vol. 9, p. 664-671, 2000). Further, when model mice with systemic lupus erythematosus pathology are subjected to genetic modification so as not to generate pDCs, the onset of systemic lupus erythematosus is inhibited. From this viewpoint, the involvement of pDCs in systemic lupus erythematosus pathology has been demonstrated directly (Proc. Natl. Acad. Sci. USA, Vol. 110, p. 2940-2945, 2013).

As an antibody against human BDCA-2, AC144 which is a mouse monoclonal antibody is known (Patent Document 1, and Non-Patent Documents 1 to 4), and it has been reported that AC144 can inhibit pDCs in the activated state by crosslinking the BDCA-2 molecules. Specifically, it has been reported that production of IFNα or the like induced from pDCs stimulated by ligand to a Toll-like receptor (TLR) 9 can be inhibited by using AC144 (Non-Patent Documents 1 to 4). It has also been reported that use of the serum from systemic lupus erythematosus patients in a stimulant induces IFNα production from pDCs, and this IFNα production can also be similarly inhibited by using AC144 (Non-Patent Document 4).

RELATED ART

Patent Document

[Patent Document 1] WO 2001/036487

Non-Patent Document

[Non-Patent Document 1] PLoS Biology (US) Sep. 11, 2007, Vol. 5, 10, p. 2190-2200
[Non-Patent Document 2] European Journal of Immunology (German) Nov. 16, 2007, Vol. 37, p. 3564-3575
[Non-Patent Document 3] Cellular Immunology (Netherlands) Jul. 6, 2010, Vol. 265, p. 15-22
[Non-Patent Document 4] The Journal of Experimental Medicine (US) Dec. 17, 2001, Vol. 194, 12, p. 1823-1834

DISCLOSURE OF INVENTION

Problems to be Solved by the Invention

An object of the present invention is to provide an anti-human BDCA-2 antibody that binds to human BDCA-2 and controls the function of pDCs through human BDCA-2 and thereby preventing or treating autoimmune disease.

Means for Solving the Problems

As a result of intensive research on preparation of an anti-human BDCA-2 antibody by the present inventors, an antibody comprising each of a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4; a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8; and a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12 was prepared (Example 5), and it was found that the antibody binds to an extracellular region of human BDCA-2 (Example 7), controls the function of pDCs through human BDCA-2, and inhibits the IFNα production from pDCs (Example 8). Therefore, the anti-human BDCA-2 antibody was provided, thereby completing the present invention.

The present invention includes the following invention as a material or a method which is medically or industrially applicable.

(1) An anti-human BDCA-2 antibody or an antigen-binding fragment thereof, selected from any one of the following 1) to 4):

1) an anti-human BDCA-2 antibody or an antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4;

2) an anti-human BDCA-2 antibody or an antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8;

3) an anti-human BDCA-2 antibody or an antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12; and 4) an anti-human BDCA-2 antibody or an antigen-binding fragment thereof, which is an antibody or an antigen-binding fragment thereof derived from posttranslational modification of the anti-human antibody or antigen-binding fragment thereof of any one of 1) to 3) above.

(2) The anti-human BDCA-2 antibody or the antigen-binding fragment thereof of (1) above, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4.

(3) The anti-human BDCA-2 antibody or the antigen-binding fragment thereof of (1) above, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8.

(4) The anti-human BDCA-2 antibody or the antigen-binding fragment thereof of (1) above, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

(5) The anti-human BDCA-2 antibody or the antigen-binding fragment thereof of (1) above, which is the antibody or the antigen-binding fragment thereof derived from posttranslational modification of the anti-human antibody or antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4.

(6) The anti-human BDCA-2 antibody or the antigen-binding fragment thereof of (1) above, which is the antibody or the antigen-binding fragment thereof derived from posttranslational modification of the anti-human antibody or antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8.

(7) The anti-human BDCA-2 antibody or the antigen-binding fragment thereof of (1) above, which is the antibody or the antigen-binding fragment thereof derived from posttranslational modification of the anti-human antibody or antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

(8) The anti-human BDCA-2 antibody or the antigen-binding fragment thereof of any one of (1) and (5) to (7) above, wherein the posttranslational modification is pyroglutamylation at the N terminal of the heavy chain variable region and/or deletion of lysine at the C terminal of the heavy chain.

(9) The anti-human BDCA-2 antibody or the antigen-binding fragment thereof of any one of (1) to (8) above, comprising a heavy chain constant region which is a human Igγ1 constant region.

(10) The anti-human BDCA-2 antibody or the antigen-binding fragment thereof of any one of (1) to (8) above, comprising a light chain constant region which is a human Igκ constant region.

(11) The anti-human BDCA-2 antibody or the antigen-binding fragment thereof of any one of (1) to (8) above, comprising a heavy chain constant region which is a human Igγ1 constant region and a light chain constant region which is a human Igκ constant region.

(12) The anti-human BDCA-2 antibody of (2) above, comprising a heavy chain consisting of the amino acid sequence shown by SEQ ID NO: 2 and a light chain consisting of the amino acid sequence shown by SEQ ID NO: 4.

(13) The anti-human BDCA-2 antibody of (3) above, comprising a heavy chain consisting of the amino acid sequence shown by SEQ ID NO: 6 and a light chain consisting of the amino acid sequence shown by SEQ ID NO: 8.

(14) The anti-human BDCA-2 antibody of (4) above, comprising a heavy chain consisting of the amino acid sequence shown by SEQ ID NO: 10 and a light chain consisting of the amino acid sequence shown by SEQ ID NO: 12.

(15) The antigen-binding fragment of any one of (1) to (11) above, which is a single-chain variable region fragment, Fab, Fab', or F(ab')$_2$.

(16) The anti-human BDCA-2 antibody, which is the antibody derived from posttranslational modification of the anti-human BDCA-2 antibody of any one of (12) to (14).

(17) The anti-human BDCA-2 antibody of (16) above, wherein the posttranslational modification is pyroglutamylation at the N terminal of the heavy chain variable region and/or deletion of lysine at the C terminal of the heavy chain.

(18) The anti-human BDCA-2 antibody of (16) above, comprising a heavy chain consisting of the amino acid sequence of the amino acid numbers 1 to 449 of SEQ ID NO: 2 in which glutamine of amino acid number 1 is modified to pyroglutamic acid and a light chain consisting of the amino acid sequence shown by SEQ ID NO: 4.

(19) The anti-human BDCA-2 antibody of (16) above, comprising a heavy chain consisting of the amino acid number of the amino acid numbers 1 to 449 of SEQ ID NO: 6, and a light chain consisting of the amino acid sequence shown by SEQ ID NO: 8.

(20) The anti-human BDCA-2 antibody of (16) above, comprising a heavy chain consisting of the amino acid sequence of the amino acid numbers 1 to 451 of SEQ ID NO: 10 in which glutamine of amino acid number 1 is modified to pyroglutamic acid and a light chain consisting of the amino acid sequence shown by SEQ ID NO: 12.

(21) A polynucleotide comprising a base sequence encoding the heavy chain variable region of the anti-human BDCA-2 antibody or the antigen-binding fragment thereof of any one of (1) to (4) above.

(22) A polynucleotide comprising a base sequence encoding the light chain variable region of the anti-human BDCA-2 antibody or the antigen-binding fragment thereof of any one of (1) to (4) above.

(23) An expression vector comprising the polynucleotide of (21) and/or (22) above.

(24) A host cell transformed with the expression vector of (23) above, selected from the group consisting of the following (a) to (d):

(a) a host cell transformed with an expression vector comprising a polynucleotide comprising a base sequence encoding the heavy chain variable region of the anti-human BDCA-2 antibody or the antigen-binding fragment thereof of any one of (1) to (4) above and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human BDCA-2 antibody or the antigen-binding fragment thereof of any one of (1) to (4) above and an expression vector comprising a polynucleotide comprising a base sequence encoding the light chain variable region of the antibody or the antigen-binding fragment thereof;

(c) a host cell transformed with an expression vector comprising a polynucleotide comprising a base sequence encoding the heavy chain variable region of the anti-human BDCA-2 antibody or the antigen-binding fragment thereof of any one of (1) to (4) above; and (d) a host cell transformed with an expression vector comprising a polynucleotide comprising a base sequence encoding the light chain variable region of the anti-human BDCA-2 antibody or the antigen-binding fragment thereof of any one of (1) to (4) above.

(25) A host cell transformed with the expression vector of (23) above, selected from the group consisting of following (a) to (d):

(a) a host cell transformed with an expression vector comprising a polynucleotide comprising a base sequence encoding the heavy chain of the anti-human BDCA-2 antibody of any one of (12) to (14) above and a polynucleotide comprising a base sequence encoding the light chain of the antibody;

(b) a host cell transformed with an expression vector comprising a polynucleotide comprising a base sequence encoding the heavy chain of the anti-human BDCA-2 antibody of any one of (12) to (14) above and an expression vector comprising a polynucleotide comprising a base sequence encoding the light chain of the antibody;

(c) a host cell transformed with an expression vector comprising a polynucleotide comprising a base sequence encoding the heavy chain of the anti-human BDCA-2 antibody of any one of (12) to (14) above; and (d) a host cell transformed with an expression vector comprising a polynucleotide comprising a base sequence encoding the light chain of the anti-human BDCA-2 antibody of any one of (12) to (14) above.

(26) A method for producing an anti-human BDCA-2 antibody or an antigen-binding fragment thereof, comprising culturing host cell(s) selected from the group consisting of following (a) to (c) to express the anti-human BDCA-2 antibody or the antigen-binding fragment thereof:

(a) a host cell transformed with an expression vector comprising a polynucleotide comprising a base sequence encoding the heavy chain variable region of the anti-human BDCA-2 antibody or the antigen-binding fragment thereof of any one of (1) to (4) above and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human BDCA-2 antibody or the antigen-binding fragment thereof of any one of (1) to (4) above and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human BDCA-2 antibody or the antigen-binding fragment thereof of any one of (1) to (4) above and a host cell transformed with an expression vector comprising a polynucleotide comprising a base sequence encoding the light chain variable region of the anti-human BDCA-2 antibody or the antigen-binding fragment thereof.

(27) A method for producing an anti-human BDCA-2 antibody, comprising culturing host cell(s) selected from the group consisting of following (a) to (c) to express the anti-human BDCA-2 antibody:

(a) a host cell transformed with an expression vector comprising a polynucleotide comprising a base sequence encoding the heavy chain of the anti-human BDCA-2 antibody of any one of (12) to (14) above and a polynucleotide comprising a base sequence encoding the light chain of the antibody;

(b) a host cell transformed with an expression vector comprising a polynucleotide comprising a base sequence encoding the heavy chain of the anti-human BDCA-2 antibody of any one of (12) to (14) above and an expression vector comprising a polynucleotide comprising a base sequence encoding the light chain of the antibody; and (c) a host cell transformed with an expression vector comprising a polynucleotide comprising a base sequence encoding the heavy chain of the anti-human BDCA-2 antibody of any one of (12) to (14) above and a host cell transformed with an expression vector comprising a polynucleotide comprising a base sequence encoding the light chain of the anti-human BDCA-2 antibody.

(28) An anti-human BDCA-2 antibody or an antigen-binding fragment thereof, produced by the method of (26) above.

(29) An anti-human BDCA-2 antibody, produced by the method of (27) above.

(30) A pharmaceutical composition comprising the anti-human BDCA-2 antibody or the antigen-binding fragment thereof of any one of (1) to (20), (28), and (29) above, and a pharmaceutically acceptable excipient.

(31) A pharmaceutical composition, comprising the anti-human BDCA-2 antibody or the antigen-binding fragment thereof of (2) above, the anti-human BDCA-2 antibody or the antigen-binding fragment thereof of (5) above, and a pharmaceutically acceptable excipient.

(32) A pharmaceutical composition, comprising the anti-human BDCA-2 antibody or the antigen-binding fragment thereof of (3) above, the anti-human BDCA-2 antibody or the antigen-binding fragment thereof of (6) above, and a pharmaceutically acceptable excipient.

(33) A pharmaceutical composition, comprising the anti-human BDCA-2 antibody or the antigen-binding fragment thereof of (4) above, the anti-human BDCA-2 antibody or the antigen-binding fragment thereof of (7) above, and a pharmaceutically acceptable excipient.

(34) The pharmaceutical composition, comprising the anti-human BDCA-2 antibody of (12) above, the anti-human BDCA-2 antibody of (18) above, and a pharmaceutically acceptable excipient.
(35) The pharmaceutical composition, comprising the anti-human BDCA-2 antibody of (13) above, the anti-human BDCA-2 antibody of (19) above, and a pharmaceutically acceptable excipient.
(36) The pharmaceutical composition, comprising the anti-human BDCA-2 antibody of (14) above, the anti-human BDCA-2 antibody of (20) above, and a pharmaceutically acceptable excipient.
(37) The pharmaceutical composition of any one of (30) to (36) above, which is a pharmaceutical composition for preventing or treating systemic lupus erythematosus.
(38) A method for preventing or treating systemic lupus erythematosus, comprising administering a therapeutically effective amount of the anti-human BDCA-2 antibody or the antigen-binding fragment thereof of any one of (1) to (20), (28), and (29) above.
(39) The anti-human BDCA-2 antibody or the antigen-binding fragment thereof of any one of (1) to (20), (28), and (29) above for use in preventing or treating systemic lupus erythematosus.
(40) Use of the anti-human BDCA-2 antibody or the antigen-binding fragment thereof of any one of (1) to (20), (28), and (29) above for manufacture of a pharmaceutical composition for preventing or treating systemic lupus erythematosus.

The anti-human BDCA-2 antibody or an antigen-binding fragment thereof includes a fusion of the antibody or the antigen-binding fragment thereof with another peptide or protein, and a modification having a modifying agent bound thereto.

Effects of the Invention

The anti-human BDCA-2 antibody of the present invention binds to an extracellular region of human BDCA-2 which is specifically expressed on the surface of pDCs and controls the function of pDCs through human BDCA-2, and can be used as an agent for preventing or treating systemic lupus erythematosus.

EMBODIMENTS FOR CARRYING OUT THE INVENTION

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG, IgM, IgA, IgD, and IgE, respectively. Further, four subclasses of IgG1, IgG2, IgG3, and IgG4 are present in IgG; and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in Igμ and Igε) and two of them are present in the light chain; one loop is formed per 100 to 110 amino acid residues, and this steric structure is similar among the loops and are referred to as a structural unit or a domain. The domain located at the N terminal side in both of the heavy chain and the light chain, whose amino acid sequence is not constant even in a case of a sample from the same class (sub class) of the same kind of animal is referred to as a variable region, and respective domains are referred to as a heavy chain variable region ($V_H$) and a light chain variable region ($V_L$). The amino acid sequence of the C terminal side from the variable region is nearly constant in each class or subclass and is referred to as a constant region (each of the domains is called $C_H1$, $C_H2$, $C_H3$ and $C_L$, respectively).

An antigenic determinant site of an antibody is configured of $V_H$ and $V_L$, and the binding specificity depends on the amino acid sequence of this site. On the other hand, biological activities such as binding to complements and various cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Further, various kinds of antigen-binding fragments comprising $V_H$ and $V_L$ of an antibody have antigen binding activity. For example, a single-chain variable region fragment (scFv), Fab, Fab', and F(ab')$_2$ are exemplified as typical antigen-binding fragments. A Fab is a monovalent antigen-binding fragment which is constituted with a light-chain and a heavy-chain fragment including a $V_H$, a $C_H1$, and a portion of the hinge region. A Fab' is a monovalent antigen-binding fragment which is constituted with a light-chain and a heavy-chain fragment including a $V_H$, a $C_H1$, and a portion of the hinge region, and cysteine residues constituting the inter-heavy-chain S—S bond are included in the portion of the hinge region. A F(ab')$_2$ is a bivalent antigen-binding fragment having a dimeric structure in which two Fab' fragments bind to each other via the inter-heavy-chain S—S bond in the hinge region. An scFv is a monovalent antigen-binding fragment which is constituted with a $V_H$ and $V_L$ connected with a linker peptide.

<Anti-Human BDCA-2 Antibody of the Present Invention>

The anti-human BDCA-2 antibody or the antigen-binding fragment thereof of the present invention includes an anti-human BDCA-2 antibody or an antigen-binding fragment thereof, having any one of the following characteristics.

1) An anti-human BDCA-2 antibody or an antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4.

2) An anti-human BDCA-2 antibody or an antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8.

3) An anti-human BDCA-2 antibody or an antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

Preferably, the anti-human BDCA-2 antibody or the antigen-binding fragment thereof of the present invention has any of the characteristics of above 1) to 3) and further comprises a heavy chain constant region and a light chain constant region. As the constant region, any subclasses of constant region (for example, a constant region of Igγ1, Igγ2, Igγ3, or Igγ4 as the heavy chain constant region and a constant region of Igλ or Igκ as the light chain constant region) can be selected, but human Igγ1 constant region is preferable as the heavy chain constant region and human Igκ constant region is preferable as a light chain constant region.

A human Igγ1 constant region includes, for example, human Igγ1 constant region consisting of the amino acid sequence of amino acid numbers 121 to 450 of SEQ ID NO: 2.

A human Igκ constant region includes, for example, human Igκ constant region consisting of the amino acid sequence of amino acid numbers 110 to 215 of SEQ ID NO: 4.

As the anti-human BDCA-2 antibody or the antigen-binding fragment thereof of the present invention, the anti-human BDCA-2 antibody or the antigen-binding fragment thereof having any of the characteristics of above 1) to 3), in which the heavy chain constant region is the human Igγ1 constant region and the light chain constant region is the human Igκ constant region is further preferable.

In one embodiment, the antigen-binding fragment of the present invention is scFv, Fab, Fab', or F(ab')$_2$.

Any person skilled in the art can construct a fusion of an antibody or an antigen-binding fragment thereof and another peptide or protein and can also construct a modification having a modifying agent bound thereto, using a known method in the field. The antibody or the antigen-binding fragment thereof of the present invention includes the antibody and the antigen-binding fragment thereof in the form of such a fusion or a modification. For example, an anti-human BDCA-2 antibody or an antigen-binding fragment thereof comprising the heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4, an anti-human BDCA-2 antibody or an antigen-binding fragment thereof comprising the heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8, or an anti-human BDCA-2 antibody or an antigen-binding fragment thereof comprising the heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12 includes a fusion of the antibody or the antigen-binding fragment thereof and another peptide or protein, and a modification having a modifying agent bound thereto. The other peptide or protein used for the fusion is not particularly limited, so long as the anti-human BDCA-2 antibody or the antigen-binding fragment thereof of the present invention as the fusion has a binding activity to an extracellular region of human BDCA-2; examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not particularly limited, so long as the anti-human BDCA-2 antibody or the antigen-binding fragment thereof as the modification has a binding activity to an extracellular region of human BDCA-2; examples thereof include polyethylene glycol, sugar chains, phospholipids, liposomes, low-molecular compounds and the like.

In one embodiment, the anti-human BDCA-2 antibody of the present invention is an anti-human BDCA-2 antibody having any one of the following characteristics i) to iii).

i) An anti-human BDCA-2 antibody comprising a heavy chain consisting of the amino acid sequence shown by SEQ ID NO: 2 and a light chain consisting of the amino acid sequence shown by SEQ ID NO: 4.

ii) An anti-human BDCA-2 antibody comprising a heavy chain consisting of the amino acid sequence shown by SEQ ID NO: 6 and a light chain consisting of the amino acid sequence shown by SEQ ID NO: 8.

iii) An anti-human BDCA-2 antibody comprising a heavy chain consisting of the amino acid sequence shown by SEQ ID NO: 10 and a light chain consisting of the amino acid sequence shown by SEQ ID NO: 12.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (Journal of Pharmaceutical Sciences, 2008, Vol. 97, p. 2426-2447).

The anti-human BDCA-2 antibody or the antigen-binding fragment thereof of the present invention includes an anti-human BDCA-2 antibody or an antigen-binding fragment thereof derived from posttranslational modification. Examples of the anti-human BDCA-2 antibody or the antigen-binding fragment thereof of the present invention, which is derived from posttranslational modification, include anti-human BDCA-2 antibodies or antigen-binding fragments thereof, which have undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, 2006, Vol. 348, p. 24-39).

The anti-human BDCA-2 antibody of the present invention includes an anti-human BDCA-2 antibody or an antigen-binding fragment thereof, having any one of the following characteristics.

(1) The anti-human BDCA-2 antibody or the antigen-binding fragment thereof derived from posttranslational modification of the anti-human BDCA-2 antibody or antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4.

(2) The anti-human BDCA-2 antibody or the antigen-binding fragment thereof derived from posttranslational modification of the anti-human BDCA-2 antibody or antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8.

(3) The anti-human BDCA-2 antibody or the antigen-binding fragment thereof derived from posttranslational modification of the anti-human BDCA-2 antibody or antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

In one embodiment, the anti-human BDCA-2 antibody of the present invention is an anti-human BDCA-2 antibody having any one of the following characteristics (1) to (3).

(1) An anti-human BDCA-2 antibody comprising a heavy chain consisting of the amino acid sequence of SEQ ID NO: 2 in which glutamine of the amino acid number 1 is modified to pyroglutamic acid and/or lysine of the amino acid number 450 is deleted in SEQ ID NO: 2 and a light chain consisting of the amino acid sequence shown by SEQ ID NO: 4.

(2) An anti-human BDCA-2 antibody comprising a heavy chain consisting of the amino acid sequence of SEQ ID NO: 6 in which glutamic acid of the amino acid number 1 is modified to pyroglutamic acid and/or lysine of the amino acid number 450 is deleted in SEQ ID NO: 6 and a light chain consisting of the amino acid sequence shown by SEQ ID NO: 8.

(3) An anti-human BDCA-2 antibody comprising a heavy chain consisting of the amino acid sequence of SEQ ID NO: 10 in which glutamine of the amino acid number 1 is modified to pyroglutamic acid and/or lysine of the amino acid number 452 is deleted in SEQ ID NO: 10 and a light chain consisting of the amino acid sequence shown by SEQ ID NO: 12.

The present invention includes an anti-human BDCA-2 antibody or an antigen-binding fragment thereof, having any of the following characteristics.

1) An anti-human BDCA-2 antibody or an antigen-binding fragment thereof, comprising a heavy chain variable region comprising CDR1 consisting of the amino acid sequence of the amino acid numbers 31 to 35 of SEQ ID NO: 2, CDR2 consisting of the amino acid sequence of the amino acid numbers 50 to 66 of SEQ ID NO: 2, and CDR3 consisting of the amino acid sequence of the amino acid numbers 99 to 109 of SEQ ID NO: 2, and a light chain variable region comprising CDR1 consisting of the amino acid sequence of the amino acid numbers 24 to 34 of SEQ ID NO: 4, CDR2 consisting of the amino acid sequence of the amino acid numbers 50 to 56 of SEQ ID NO: 4, and CDR3 consisting of the amino acid sequence of the amino acid numbers 89 to 98 of SEQ ID NO: 4.

2) An anti-human BDCA-2 antibody or an antigen-binding fragment thereof, comprising a heavy chain variable region comprising CDR1 consisting of the amino acid sequence of the amino acid numbers 31 to 35 of SEQ ID NO: 6, CDR2 consisting of the amino acid sequence of the amino acid numbers 50 to 66 of SEQ ID NO: 6, and CDR3 consisting of the amino acid sequence of the amino acid numbers 99 to 109 of SEQ ID NO: 6, and a light chain variable region comprising CDR1 consisting of the amino acid sequence of the amino acid numbers 24 to 34 of SEQ ID NO: 8, CDR2 consisting of the amino acid sequence of the amino acid numbers 50 to 56 of SEQ ID NO: 8, and CDR3 consisting of the amino acid sequence of the amino acid numbers 89 to 97 of SEQ ID NO: 8.

3) An anti-human BDCA-2 antibody or an antigen-binding fragment thereof, comprising a heavy chain variable region comprising CDR1 consisting of the amino acid sequence of the amino acid numbers 31 to 37 of SEQ ID NO: 10, CDR2 consisting of the amino acid sequence of the amino acid numbers 52 to 67 of SEQ ID NO: 10, and CDR3 consisting of the amino acid sequence of the amino acid numbers 100 to 111 of SEQ ID NO: 10, and a light chain variable region comprising CDR1 consisting of the amino acid sequence of the amino acid numbers 24 to 34 of SEQ ID NO: 12, CDR2 consisting of the amino acid sequence of the amino acid numbers 50 to 56 of SEQ ID NO: 12, and CDR3 consisting of the amino acid sequence of the amino acid numbers 89 to 97 of SEQ ID NO: 12.

The anti-human BDCA-2 antibody or the antigen-binding fragment thereof of the present invention binds to an extracellular region of human BDCA-2 (consisting of the amino acid sequence of the amino acid numbers 42 to 213 of SEQ ID NO: 13). Whether the anti-human BDCA-2 antibody or an antigen-bonded fragment thereof binds to an extracellular region of human BDCA-2 is confirmed by using a known binding activity measurement method. Examples of the binding activity measurement method include a method of Enzyme-Linked ImmunoSorbent Assay (ELISA) or the like. In a case of using the ELISA, in an exemplary method, cells (for example, CHO-K1 cells) in which human BDCA-2 (SEQ ID NO: 13) or human BDCA-2 variant (SEQ ID NO: 15) as described in Example 3 below is expressed are seeded on an ELISA plate, and a test antibody is added thereto to be reacted. After the reaction, a secondary antibody such as an anti-IgG antibody, labeled with an enzyme such as horseradish peroxidase (HRP) or the like, is reacted, and washed off, and then it is possible to confirm whether the test antibody binds to an extracellular region of human BDCA-2 by activity measurement using a reagent (for example, in a case of HRP labeling, BM-Chemiluminescence ELISA Substrate (POD) (Roche Diagnostics. Inc.)).

Further, the anti-human BDCA-2 antibody or the antigen-binding fragment thereof of the present invention includes an antibody or an antigen-binding fragment thereof binding to an extracellular region of human BDCA-2, which is an antibody or an antigen-binding fragment thereof binding to an extracellular region of BDCA-2 derived from other animals (for example, monkey BDCA-2), in addition to binding to the extracellular region of human BDCA-2.

In addition, the anti-human BDCA-2 antibody or an antigen-binding fragment thereof of the present invention binds to an extracellular region of human BDCA-2 and has an inhibitory activity on IFNα production. As a specific method for evaluating the inhibitory activity on IFNα production, the same method as described in Example 4 described later can be used.

The anti-human BDCA-2 antibody or the antigen-binding fragment thereof of the present invention can be easily prepared by a person skilled in the art using a known method in the field, based on sequence information on the heavy chain variable region and the light chain variable region of the anti-human BDCA-2 antibody of the invention, which is disclosed in the present specification. The anti-human BDCA-2 antibody or the antigen-binding fragment thereof of the present invention is not particularly limited, but can be produced according to the method described in the section of <Method of producing anti-human BDCA-2 receptor antibody of the present invention, and anti-human BDCA-2 antibody produced by the method> described below.

The anti-human BDCA-2 antibody or the antigen-binding fragment thereof of the present invention is further purified as needed, and formulated according to a conventional method. It may be used for the prevention or the treatment of diseases in which pDCs are involved with disease pathology, including autoimmune diseases such as systemic lupus erythematosus, scleroderma, polymyositis and dermatomyositis, psoriasis, Sjogren's syndrome, rheumatoid arthritis, Grave's disease, and Hashimoto's disease.

<Polynucleotide of the Present Invention>

The polynucleotide of the present invention includes a polynucleotide comprising a base sequence encoding the heavy chain variable region of the anti-human BDCA-2 antibody or the antigen-binding fragment thereof of the present invention and a polynucleotide comprising a base sequence encoding the light chain variable region of the anti-human BDCA-2 antibody or the antigen-binding fragment thereof of the present invention.

In one embodiment, the polynucleotide comprising a base sequence encoding the heavy chain variable region of the anti-human BDCA-2 antibody or the antigen-binding fragment thereof of the present invention is a polynucleotide comprising a base sequence encoding the heavy chain variable region consisting of the amino acid sequence of amino acid numbers 1 to 120 of SEQ ID NO: 2, a polynucleotide comprising a base sequence encoding the heavy chain variable region consisting of the amino acid sequence of amino acid numbers 1 to 120 of SEQ ID NO: 6, or a polynucleotide comprising a base sequence encoding the heavy chain variable region consisting of the amino acid sequence of amino acid numbers 1 to 122 of SEQ ID NO: 10.

Examples of the polynucleotide comprising the base sequence encoding the heavy chain variable region shown by the amino acid sequence of the amino acid numbers 1 to 120 of SEQ ID NO: 2 include a polynucleotide comprising the base sequence of the base numbers 1 to 360 of SEQ ID NO: 1. Examples of the polynucleotide comprising the base sequence encoding the heavy chain variable region consisting of the amino acid sequence of the amino acid numbers 1 to 120 of SEQ ID NO: 6 include a polynucleotide comprising the base sequence of the base numbers 1 to 360 of SEQ ID NO: 5. Examples of the polynucleotide comprising the base sequence encoding the heavy chain variable region consisting of the amino acid sequence of the amino acid numbers 1 to 122 of SEQ ID NO: 10 include a polynucleotide comprising the base sequence of the base numbers 1 to 366 of SEQ ID NO: 9.

In a preferred embodiment, the polynucleotide comprising a base sequence encoding the heavy chain variable region of the anti-human BDCA-2 antibody of the present invention is a polynucleotide comprising the base sequence encoding the heavy chain consisting of the amino acid sequence shown by SEQ ID NO: 2, a polynucleotide comprising the base sequence encoding the heavy chain consisting of the amino acid sequence shown by SEQ ID NO: 6, or a polynucleotide comprising the base sequence encoding the heavy chain consisting of the amino acid sequence shown by SEQ ID NO: 10.

Examples of the polynucleotide comprising the base sequence encoding the heavy chain consisting of the amino acid sequence shown by SEQ ID NO: 2 include a polynucleotide comprising the base sequence shown by SEQ ID NO: 1. Examples of the polynucleotide comprising the base sequence encoding the heavy chain consisting of the amino acid sequence shown by SEQ ID NO: 6 include a polynucleotide comprising the base sequence shown by SEQ ID NO: 5. Examples of the polynucleotide comprising the base sequence encoding the heavy chain consisting of the amino acid sequence shown by SEQ ID NO: 10 include a polynucleotide comprising the base sequence shown by SEQ ID NO: 9.

In one embodiment, the polynucleotide comprising the base sequence encoding the light chain variable region of the anti-human BDCA-2 antibody or the antigen-binding fragment thereof of the present invention is a polynucleotide comprising a base sequence encoding the light chain variable region consisting of the amino acid sequence of amino acid numbers 1 to 109 of SEQ ID NO: 4, a polynucleotide comprising a base sequence encoding the light chain variable region consisting of the amino acid sequence of amino acid numbers 1 to 108 of SEQ ID NO: 8, or a polynucleotide comprising a base sequence encoding the light chain variable region consisting of the amino acid sequence of amino acid numbers 1 to 108 of SEQ ID NO: 12.

Examples of the polynucleotide comprising the base sequence encoding the light chain variable region consisting of the amino acid sequence of amino acid numbers 1 to 109 of SEQ ID NO: 4 include a polynucleotide comprising a base sequence of the base numbers 1 to 327 of SEQ ID NO: 3. Examples of the polynucleotide comprising the base sequence encoding the light chain variable region consisting of the amino acid sequence of amino acid numbers 1 to 108 of SEQ ID NO: 8 include a polynucleotide comprising a base sequence of the base numbers 1 to 324 of SEQ ID NO: 7. Examples of the polynucleotide comprising the base sequence encoding the light chain variable region consisting of the amino acid sequence of amino acid numbers 1 to 108 of SEQ ID NO: 12 include a polynucleotide comprising a base sequence of the base numbers 1 to 324 of SEQ ID NO: 11.

In a preferred embodiment, the polynucleotide comprising the base sequence encoding the light chain variable region of the anti-human BDCA-2 antibody of the present invention is a polynucleotide comprising a base sequence encoding the light chain consisting of the amino acid sequence shown by SEQ ID NO: 4, a polynucleotide comprising a base sequence encoding the light chain consisting of the amino acid sequence shown by SEQ ID NO: 8, or a polynucleotide comprising a base sequence encoding the light chain consisting of the amino acid sequence shown by SEQ ID NO: 12.

Examples of the polynucleotide comprising the base sequence encoding the light chain consisting of the amino acid sequence shown by SEQ ID NO: 4 include a polynucleotide comprising the base sequence shown by SEQ ID NO: 3. Examples of the polynucleotide comprising the base sequence encoding the light chain consisting of the amino acid sequence shown by SEQ ID NO: 8 include a polynucleotide comprising the base sequence shown by SEQ ID NO: 7. Examples of the polynucleotide comprising the base sequence encoding the light chain consisting of the amino acid sequence shown by SEQ ID NO: 12 include a polynucleotide comprising the base sequence shown by SEQ ID NO: 11.

The polynucleotide of the present invention can be easily prepared by a person skilled in the art using a known method in the field based on the base sequence. For example, the polynucleotide of the present invention can be synthesized using a known gene synthesis method in the field. As the gene synthesis method, various methods such as a synthesis method of antibody genes described in WO90/07861 known by a person skilled in the art can be used.

<Expression Vector of the Present Invention>

An expression vector of the present invention includes an expression vector comprising the polynucleotide comprising the base sequence encoding the heavy chain variable region of the anti-human BDCA-2 antibody or the antigen-binding fragment thereof of the present invention and/or the polynucleotide comprising the base sequence encoding the light chain variable region of the anti-human BDCA-2 antibody or the antigen-binding fragment thereof of the present invention.

Preferred expression vectors of the present invention include an expression vector comprising a polynucleotide comprising the base sequence encoding the heavy chain of the anti-human BDCA-2 antibody of the present invention, an expression vector comprising a polynucleotide comprising the base sequence encoding the light chain of the anti-human BDCA-2 antibody of the present invention, or an expression vector comprising a polynucleotide comprising the base sequence encoding the heavy chain of the anti-human BDCA-2 antibody of the present invention and a polynucleotide comprising the base sequence encoding the light chain of the antibody.

The expression vector used to express the polynucleotide of the present invention are not particularly limited as long as a polynucleotide comprising the base sequence encoding the heavy chain variable region of the anti-human BDCA-2 antibody or the antigen-binding fragment thereof of the present invention and/or a polynucleotide comprising the base sequence encoding the light chain variable region of the anti-human BDCA-2 antibody or the antigen-binding fragment thereof of the present invention can be expressed in various host cells of eukaryotic cells (for example, animal cells, insect cells, plant cells, and yeast) and/or prokaryotic cells (for example, $Escherichia\ coli$), and the polypeptides encoded by these can be produced. Examples of the expression vector include plasmid vectors, viral vectors (for example, adenovirus or retrovirus), and the like. Preferably pEE6.4 or pEE12.4 (Lonza, Inc.) can be used. Further, antibody genes can be expressed by transferring a variable region gene fragment to expression vectors comprising human Ig constant region genes such as AG-γ1 or AG-κ (for example, see WO94/20632) in advance.

The expression vector of the present invention may include a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) 1α promoter, and a heat shock promoter. Examples of promoters for expression by bacteria (for example, $Escherichia$) include a trp promoter, a lac promoter, λPL promoter, and tac promoter. Further, examples of promoters for expression by yeast include a GAL1 promoter, a GAL10 promoter, a PH05 promoter, a PGK promoter, a GAP promoter, and an ADH promoter.

In the case of using an animal cell, an insect cell, or yeast as the host cell, the expression vector of the present invention may comprise start codon and stop codon. In this case, the expression vector of the present invention may comprise an enhancer sequence, an untranslated region on the 5' side and the 3' side of genes encoding the antibody of the present invention or the heavy chain variable region or the light chain variable region, a secretory signal sequence, a splicing junction, a polyadenylation site, or a replicable unit. When $Escherichia\ coli$ is used as the host cell, the expression vector of the present invention may comprise a start codon, a stop codon, a terminator region, and a replicon. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the necessity.

<Transformed Host Cell of the Present Invention>

The transformed host cell of the present invention includes a host cell transformed with the expression vector of the present invention which is selected from the group consisting of the following (a) to (d):

(a) a host cell transformed with an expression vector comprising the polynucleotide comprising the base sequence encoding the heavy chain variable region of the anti-human BDCA-2 antibody or the antigen-binding fragment thereof of the present invention and the polynucleotide comprising the base sequence encoding the light chain variable region of the antibody or the antigen-binding fragment thereof;

(b) a host cell transformed with an expression vector comprising the polynucleotide comprising the base sequence encoding the heavy chain variable region of the anti-human BDCA-2 antibody or the antigen-binding fragment thereof of the present invention and an expression vector comprising the polynucleotide comprising the base sequence encoding the light chain variable region of the antibody or the antigen-binding fragment thereof;

(c) a host cell transformed with an expression vector comprising the polynucleotide comprising the base sequence encoding the heavy chain variable region of the anti-human BDCA-2 antibody or the antigen-binding fragment thereof of the present invention; and (d) a host cell transformed with an expression vector comprising the polynucleotide comprising the base sequence encoding the light chain variable region of the anti-human BDCA-2 antibody or the antigen-binding fragment thereof of the present invention.

In one embodiment, the transformed host cell of the present invention is a host cell transformed with the expression vector of the present invention which is selected from the group consisting of the following (a) to (d):

(a) a host cell transformed with an expression vector comprising a polynucleotide comprising the base sequence encoding the heavy chain of the anti-human BDCA-2 antibody of the present invention and a polynucleotide comprising the base sequence encoding the light chain of the antibody;

(b) a host cell transformed with an expression vector comprising a polynucleotide comprising the base sequence encoding the heavy chain of the anti-human BDCA-2 antibody of the present invention and an expression vector comprising a polynucleotide comprising the base sequence encoding the light chain of the antibody;

(c) a host cell transformed with an expression vector comprising a polynucleotide comprising the base sequence encoding the heavy chain of the anti-human BDCA-2 antibody of the present invention; and (d) a host cell transformed with an expression vector comprising a polynucleotide comprising the base sequence encoding the light chain of the anti-human BDCA-2 antibody of the present invention.

Preferred examples of the transformed host cell of the present invention include a host cell transformed with an expression vector comprising a polynucleotide comprising the base sequence encoding the heavy chain of the anti-human BDCA-2 antibody of the present invention and a polynucleotide comprising the base sequence encoding the light chain of the antibody, and a host cell transformed with an expression vector comprising a polynucleotide comprising the base sequence encoding the heavy chain of the anti-human BDCA-2 antibody of the present invention and an expression vector comprising a polynucleotide comprising the base sequence encoding the light chain of the antibody.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). Preferably cultured cells such as CHO-K1SV cells, CHO-DG 44 cells, 293 cells, or NSO cells can be used.

A method of transforming the host cell is not particularly limited, but, for example, a calcium phosphate method or an electroporation method can be used.

<Method of Producing Anti-Human BDCA-2 Antibody of the Present Invention, and Anti-Human BDCA-2 Antibody Produced by the Method>

Examples of the method for producing the anti-human BDCA-2 antibody or the antigen-binding fragment thereof of the present invention include a method for producing an anti-human BDCA-2 antibody or an antigen-binding fragment thereof, comprising culturing host cell(s) selected from the group consisting of following (a) to (c) to express the anti-human BDCA-2 antibody or the antigen-binding fragment thereof:

(a) a host cell transformed with an expression vector comprising a polynucleotide comprising a base sequence encoding the heavy chain variable region of the anti-human BDCA-2 antibody or the antigen-binding fragment thereof of the present invention and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human BDCA-2 antibody or the antigen-binding fragment thereof of the present invention and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human BDCA-2 antibody or the antigen-binding fragment thereof of the present invention and a host cell transformed with an expression vector comprising a polynucleotide comprising a base sequence encoding the light chain variable region of the antibody or the antigen-binding fragment thereof.

In one embodiment, examples of the method for producing the anti-human BDCA-2 antibody of the present invention include a method for producing an anti-human BDCA-2 antibody, comprising culturing host cell(s) selected from the group consisting of following (a) to (c) to express the anti-human BDCA-2 antibody:

(a) a host cell transformed with an expression vector comprising a polynucleotide comprising a base sequence encoding the heavy chain of the anti-human BDCA-2 antibody of the present invention and a polynucleotide comprising a base sequence encoding the light chain of the antibody;

(b) a host cell transformed with an expression vector comprising a polynucleotide comprising a base sequence encoding the heavy chain of the anti-human BDCA-2 antibody of the present invention and an expression vector comprising a polynucleotide comprising a base sequence encoding the heavy chain of the antibody; and (c) a host cell transformed with an expression vector comprising a polynucleotide comprising a base sequence encoding the heavy chain of the anti-human BDCA-2 antibody of the present invention and a host cell transformed with an expression vector comprising a polynucleotide comprising a base sequence encoding the light chain of the antibody.

The method for producing the anti-human BDCA-2 antibody or the antigen-binding fragment thereof of the present invention is not particularly limited as long as it includes a step of culturing the transformed host cells of the present invention to express the anti-human BDCA-2 antibody or an antigen-binding fragment thereof. Examples of the preferred host cells used in the method include the preferred transformed host cells of the present invention as described above.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, 1959, Vol. 130, No. 3373, p. 432 to 7), DMEM culture medium (Virology, 1959, Vol. 8, p. 396), and RPMI1640 culture medium (J. Am. Med. Assoc., 1967, Vol. 199, p. 519), a 199 culture medium (Exp. Biol. Med., 1950, Vol. 73, p. 1 to 8). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, as the culture medium, for example, Grace's culture medium (Proc. Natl. Acad. Sci. USA, 1985, Vol. 82, p. 8404) supplemented with fetal bovine serum can be used. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. It is preferable that the nutrient culture medium include a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, Vol. 3, A2.2). The culture is generally carried out at approximately 14° C. to 39° C. for approximately 3 hours to 24 hours while air ventilating and stirring if necessary. In a case where the host cell is yeast, as the culture medium, for example, Burkholder minimal medium (Proc. Natl. Acad, Sci, USA, 1980, Vol. 77, p. 4505) can be used. The culture is generally carried out at approximately 20° C. to 35° C. for approximately 14 hours to 144 hours while air ventilating and stirring if necessary. By carrying out the culture in the above-described manner, it is possible to express the anti-human BDCA-2 antibody or the antigen-binding fragment thereof of the present invention.

The method of producing the anti-human BDCA-2 antibody or the antigen-binding fragment thereof of the present invention may include obtaining, preferably isolating or purifying the anti-human BDCA-2 antibody or the antigen-binding fragment thereof from the transformed host cell in addition to culturing the transformed host cell of the present invention to express the anti-human BDCA-2 antibody or the antigen-binding fragment thereof. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. Preferably, the antibody accumulated in a culture supernatant can be purified by various chromatographies, for example, column chromatography using Protein A column or Protein G column.

The anti-human BDCA-2 antibody or the antigen-binding fragment thereof of the present invention also includes an anti-human BDCA-2 antibody or an antigen-binding fragment thereof produced by the method for producing the anti-human BDCA-2 antibody or the antigen-binding fragment thereof of the present invention.

<Pharmaceutical Composition of the Present Invention>

The pharmaceutical compositions of the present invention include a pharmaceutical composition comprising the anti-human BDCA-2 antibody or the antigen-binding fragment thereof of the present invention and pharmaceutically acceptable excipients. The pharmaceutical composition of the present invention can be prepared by a method being generally used with excipients, that is, excipients for medicine or carriers for medicine being generally used in the field. Examples of dosage forms of the pharmaceutical compositions include parenteral drug such as an injection drug and a drip infusion drug, and these can be administered by intravenous administration, subcutaneous administration, or the like. In drug preparation, excipients, carriers, and additives in accordance with the dosage forms can be used within the pharmaceutically acceptable range.

The pharmaceutical compositions of the present invention may include plural kinds of anti-human BDCA-2 antibodies or antigen-binding fragments thereof of the present invention. For example, the present invention includes a pharmaceutical composition comprising an antibody or an antigen-binding fragment thereof, which does not undergo posttranslational modification and an antibody or an antigen-binding fragment thereof derived from posttranslational modification of the antibody or the antigen-binding fragment thereof.

In one embodiment, the pharmaceutical composition of the present invention, comprising an anti-human BDCA-2 antibody or an antigen-binding fragment thereof, includes a pharmaceutical composition of any one of the following (1) to (3).

(1) A pharmaceutical composition comprising an anti-human BDCA-2 antibody or the antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4, and an antibody or an antigen-binding fragment thereof which is derived from posttranslational modification of the antibody or the antigen-binding fragment thereof.

(2) A pharmaceutical composition comprising an anti-human BDCA-2 antibody or the antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8, and an antibody or an antigen-binding fragment thereof which is derived from posttranslational modification of the antibody or the antigen-binding fragment thereof.

(3) A pharmaceutical composition comprising an anti-human BDCA-2 antibody or the antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12, and an antibody or an antigen-binding fragment thereof which is derived from posttranslational modification of the antibody or the antigen-binding fragment thereof.

The pharmaceutical compositions of the present invention include a pharmaceutical composition comprising an antibody in which lysine of the C terminal of the heavy chain is deleted, an antibody or an antigen-binding fragment thereof with posttranslational modification to N terminal, an antibody in which lysine of the C terminal of the heavy chain is deleted and post-translation modification to N terminal is made, and/or an antibody which has lysine of the C terminal of the heavy chain and does not have posttranslational modification to N terminal.

In one embodiment, the pharmaceutical composition of the present invention, comprising an anti-human BDCA-2 antibody, includes a pharmaceutical composition comprising at least two kinds of anti-human BDCA-2 antibodies selected from following (1) to (4).

(1) An anti-human BDCA-2 antibody comprising a heavy chain consisting of the amino acid sequence of the amino acid numbers 1 to 449 of SEQ ID NO: 2 and a light chain consisting of the amino acid sequence shown by SEQ ID NO: 4.

(2) An anti-human BDCA-2 antibody comprising a heavy chain consisting of the amino acid sequence of SEQ ID NO: 2 in which glutamic acid of amino acid number 1 is modified to pyroglutamic acid and a light chain consisting of the amino acid sequence shown by SEQ ID NO: 4.

(3) An anti-human BDCA-2 antibody comprising a heavy chain consisting of the amino acid sequence of the amino acid numbers 1 to 449 of SEQ ID NO: 2 in which glutamic acid of amino acid number 1 is modified to pyroglutamic acid and a light chain consisting of the amino acid sequence shown by SEQ ID NO: 4.

(4) An anti-human BDCA-2 antibody comprising a heavy chain consisting of the amino acid sequence shown by SEQ ID NO: 2 and a light chain consisting of the amino acid sequence shown by SEQ ID NO: 4.

In one embodiment, the pharmaceutical composition of the present invention, comprising an anti-human BDCA-2 antibody, includes a pharmaceutical composition comprising at least two kinds of anti-human BDCA-2 antibodies selected from following (1) to (4).

(1) An anti-human BDCA-2 antibody comprising a heavy chain consisting of the amino acid sequence of the amino acid numbers 1 to 449 of SEQ ID NO: 6 and a light chain consisting of the amino acid sequence shown by SEQ ID NO: 8.

(2) An anti-human BDCA-2 antibody comprising a heavy chain consisting of the amino acid sequence of SEQ ID NO: 6 in which glutamine of amino acid number 1 is modified to pyroglutamic acid and a light chain consisting of the amino acid sequence shown by SEQ ID NO: 8.

(3) An anti-human BDCA-2 antibody comprising a heavy chain consisting of the amino acid sequence of the amino acid numbers 1 to 449 of SEQ ID NO: 6 in which glutamine of amino acid number 1 is modified to pyroglutamic acid and a light chain consisting of the amino acid sequence shown by SEQ ID NO: 8.

(4) An anti-human BDCA-2 antibody comprising a heavy chain consisting of the amino acid sequence shown by SEQ ID NO: 6 and a light chain consisting of the amino acid sequence shown by SEQ ID NO: 8.

In one embodiment, the pharmaceutical composition of the present invention, comprising an anti-human BDCA-2 antibody, includes a pharmaceutical composition comprising at least two kinds of anti-human BDCA-2 antibodies selected from following (1) to (4).

(1) An anti-human BDCA-2 antibody comprising a heavy chain consisting of the amino acid sequence of the amino acid numbers 1 to 451 of SEQ ID NO: 10 and a light chain consisting of the amino acid sequence shown by SEQ ID NO: 12.

(2) An anti-human BDCA-2 antibody comprising a heavy chain consisting of the amino acid sequence of SEQ ID NO: 10 in which glutamine of amino acid number 1 is modified to pyroglutamic acid and a light chain consisting of the amino acid sequence shown by SEQ ID NO: 12.

(3) An anti-human BDCA-2 antibody comprising a heavy chain consisting of the amino acid sequence of the amino acid numbers 1 to 451 of SEQ ID NO: 10 in which glutamine of amino acid number 1 is modified to pyroglutamic acid and a light chain consisting of the amino acid sequence shown by SEQ ID NO: 12.

(4) An anti-human BDCA-2 antibody comprising a heavy chain consisting of the amino acid sequence shown by SEQ ID NO: 10 and a light chain consisting of the amino acid sequence shown by SEQ ID NO: 12.

The addition amount of the anti-human BDCA-2 antibody or the antigen-binding fragment thereof of the present invention in a formulation varies depending on the degree of a patient's symptoms, the age of a patient, a dosage form of the drug to be used, the binding titer of the antibody, or the like, and for example, an addition amount of approximately 0.001 mg/kg to 100 mg/kg can be used.

The pharmaceutical composition of the present invention can be used as a pharmaceutical composition for preventing or treating diseases in which pDCs are involved in disease pathology, such as systemic lupus erythematosus.

The present invention includes a pharmaceutical composition for preventing or treating systemic lupus erythematosus, comprising the anti-human BDCA-2 antibody or the antigen-binding fragment thereof of the present invention and a pharmaceutically acceptable excipient. Further, the present invention includes a method for preventing or treating systemic lupus erythematosus, comprising administering a therapeutically effective amount of the anti-human BDCA-2 antibody or the antigen-binding fragment thereof of the present invention. Further, the present invention includes the anti-human BDCA-2 antibody or the antigen-binding fragment thereof of the present invention for use in preventing or treating systemic lupus erythematosus. In addition, the present invention includes use of the anti-human BDCA-2 antibody or the antigen-binding fragment thereof of the present invention for manufacture of a pharmaceutical composition for preventing or treating systemic lupus erythematosus.

The present invention has been described and specific examples referred to for better understanding will be provided, but these are merely examples and the present invention is not limited thereto.

EXAMPLES

With regard to parts using commercially available kits or reagents, the tests are performed according to the attached protocol unless otherwise noted.

Example 1

Acquisition of Human BDCA-2 Variant Expressing CHO-K1 Cell

For use in a binding test of an anti-human BDCA-2 antibody, a human BDCA-2 variant expressing CHO-K1 cell was acquired. Specifically, a gene (SEQ ID NO: 14) encoding a human BDCA-2 variant (SEQ ID NO: 15: consisting of the amino acid sequence having serine of the amino acid number 33 of a wild type human BDCA-2 (SEQ ID NO: 13) substituted with cysteine, in which the variation site exists in a transmembrane region, and therefore, the amino acid sequence of the extracellular region is the same as for the wild type) amplified by a PCR method was inserted into a pIRES vector (Clontech Laboratories, Inc.) which is a vector for mammal cell expression, together with a gene (SEQ ID NO: 16) encoding a full-length sequence of human FcεRIγ, thereby preparing a vector which expresses the human BDCA-2 variant and the human FcεRIγ simultaneously. Next, this vector was gene-transferred to CHO-K1 cells using a transfection reagent Lipofectamine 2000 (Life Technologies, Inc.). These cells were selectively cultured in a Geneticin (Life Technologies, Inc.)-containing RPMI1640 culture medium and then a cell population highly expressing a human BDCA-2 variant protein was further screened (hereinafter referred to as human BDCA-2 variant/CHO cells) using a cell sorter, FACSAria™ (Becton, Dickinson and Company).

Example 2

Preparation of Hybridoma Producing Anti-Human BDCA-2 Antibody

A human monoclonal antibody development technology "VelocImmune" (VelocImmune antibody technology: Regeneron, Inc. (U.S. Pat. No. 6,596,541)) mouse was used to prepare an antibody. Specifically, a fusion protein of an extracellular region of human BDCA-2 and mouse Fc, and human BDCA-2 expressing CHO-K1 cells, or a fusion protein of an extracellular region of human BDCA-2 and mouse Fc, a fusion protein of an extracellular region of monkey BDCA-2 and mouse Fc, and human BDCA-2 expression CHO-K1 cells were injected into the VelocImmune mouse, together with an adjuvant for causing an immune reaction, to perform immunization.

Thereafter, according to the conventional method, a spleen or a lymph node of the immunized mouse was extracted, and lymphocytes were collected and cell-fused with mouse myeloma cells SP2/0-Ag14, thereby preparing hybridomas. The hybridomas were monocloned and each clone was cultured in a serum-free culture medium. The antibody was purified from the obtained culture supernatants. The antibody obtained using the VelocImmune technology is an antibody having a variable region of the human antibody and a constant region of the mouse antibody (also referred to a chimeric antibody).

Example 3

Cell ELISA Binding Assay

In order to measure the antigen-specific binding activity of the antibody, the binding of the antibody to the human BDCA-2 variant/CHO cells prepared in Example 1 was evaluated. Specifically, the human BDCA-2 variant/CHO cells were first suspended in an RPMI1640 culture medium (Life Technologies, Inc.) at $2 \times 10^5$ cells/mL, seeded at 50 µL per well in a poly-D-lysine-coated 384-well plate (Greiner Bio-One), and cultured overnight in a $CO_2$ incubator set at 37° C. Then, the culture medium was removed, and 20 µL of each of a hybridoma-derived antibody (the antibody purified in Example 2) and a comparative antibody which had been diluted stepwise from a concentration of 10000 ng/mL to 4.6 ng/mL (8 steps in a 3-fold dilution series) with a diluent solution (a Hank's Balanced Salt solution supplemented with 1% bovine serum albumin) was added thereto and reacted at room temperature for 1 hour. Next, the assay plate was washed with a washing solution (a Hank's Balanced Salt solution supplemented with 0.1% bovine serum albumin) and 20 µL of an HRP-labeled rabbit anti-mouse IgG antibody (HRP-rabbit anti-human IgG antibody: Dako Ltd.) which had been diluted 5000-fold with a diluent solution was added thereto, and reacted at room temperature for 30 minutes. Thereafter, the assay plate was washed with a washing solution, 30 µL of BM-Chemiluminescence ELISA Substrate (POD) (Roche Diagnostics. Inc.) which is a chemiluminescence detection reagent was added thereto, and the amount of chemiluminescence thereof was measured by an EnVision counter (PerkinElmer, Inc.). For the measurement results, the EC50 values were determined by fitting a four-parameter logistic curve. In this test, as a comparative antibody, AC144 (Non-Patent Documents 1 to 4, Miltenyi Biotec) which is a mouse antibody against human BDCA-2 was used.

As a result, it was revealed that the antibodies (chimeric antibodies) referred to as BDC3-12A2, BDC3-12F5, and BDC13-32E3 had high binding activities against the extracellular regions of human BDCA-2 (Table 1).

TABLE 1

Binding Activities of anti-human BDCA-2 antibodies against Extracellular Regions of Human BDCA-2

|  | EC50 (ng/mL) |
| --- | --- |
| BDC3-12A2 (chimeric) | 59 |
| BDC3-12F5 (chimeric) | 57 |
| BDC13-32E3 (chimeric) | 96 |
| AC144 | 133 |

Example 4

Evaluation of Inhibitory Activity on Human IFNα Production

When a TLR9 ligand such as ODN2216 is added to human peripheral blood mononuclear cells and cultured, pDCs existing in human peripheral blood mononuclear cells are activated, and IFNα production is induced from pDCs (Non-Patent Document 1). Accordingly, the production inhibition of IFNα produced from pDCs by the anti-human BDCA-2 antibody was used as an index, and the function control activity of the antibody on pDCs was evaluated. Specifically, ODN2216 (Invivogen) prepared to have a concentration of 1.6 µM using an RPMI1640 culture medium was added to a 96-well plate with U-bottom (Greiner Bio-One) in an amount of 25 µL, and then, 25 µL of each of a hybridoma-derived antibody and a comparative antibody which had been diluted in 11 steps in a range from 4000 ng/mL to 0.02 ng/mL using an RPMI1640 culture medium was added thereto. 50 µL of human peripheral blood mononuclear cells (Lonza, Inc.) which had been suspended in an RPMI1640 culture medium containing 20 ng/mL of human IL-3 (PeproTech Inc.) at $2 \times 10^6$ cells/mL was added thereto. As a control, each of a well to which the RPMI1640 culture medium had been added instead of the antibody and a well to which the RPMI1640 culture medium had been added instead of ODN2216 was prepared. After culturing in a $CO_2$ incubator set at 37° C. for 20 hours, the amount of IFNα protein in the supernatant was quantified using an AlphaLISA IFNα assay kit (PerkinElmer, Inc.). Further, based on the quantified values, the inhibitory rate on IFNα production was calculated. More specifically, a group in which an RPMI1640 culture medium was added instead of the antibody was set as a 0% inhibition control group and a group in which an RPMI1640 culture medium was added instead of ODN2216 was set as a 100% inhibition control group. The inhibitory rate on IFNα production thus calculated was analyzed, and the IC50 value and the IC90 value of the antibody were calculated by fitting a four parameter logistic curve. The IC90 value is a minimum value with which the maximum action of each antibody can be expected, that is, a value close to a minimum value of the antibody concentration required for complete inhibition of the IFNα production from human peripheral blood mononuclear cells. It has been reported that in a systemic lupus erythematosus pathology model mouse, a trace amount of IFNα causes deterioration of pathology (The Journal of Immunology, Vol. 174, p. 2499, 2005), and it has been suggested that complete inhibition of IFNα is important for prevention and treatment of systemic lupus erythematosus. In addition, in the present Example, AC144 was used as a comparative antibody.

As a result, it became clear that BDC3-12A2, BDC3-12F5, and BDC13-32E3 had higher IFNα production inhibitory activities in both of the IC50 value and the IC90 value than the comparative antibody AC144 (Table 2). In addition, it became clear that the concentration of BDC3-12A2, BDC3-12F5, and BDC13-32E3 was lower than that of the comparative AC144 for complete inhibition of IFNα production from the IC90 value.

TABLE 2

Inhibitory Activity of Anti-Human BDCA-2 Antibody on Human IFNα Production

|  | IC50 (ng/mL) | IC90 (ng/mL) |
| --- | --- | --- |
| BDC3-12A2 (chimeric) | 0.27 | 1.03 |
| BDC3-12F5 (chimeric) | 0.23 | 0.93 |
| BDC13-32E3 (chimeric) | 0.43 | 1.03 |
| AC144 | 2.57 | 56.5 |

Example 5

Sequencing and Preparation of Fully Human Anti-Human BDCA-2 Antibody

From the hybridomas each producing BDC3-12A2, BDC3-12F5, and BDC13-32E3, genes encoding the heavy chain and the light chain of the antibody were cloned and sequenced.

In the above-described antibody, the variable region is human-derived and the constant region is mouse-derived. Therefore, expression vectors comprising both genes of the heavy chain and the light chain were constructed using a GS Gene Expression System (Lonza, Inc.) and a fully human antibody in which a variable region and a constant region are human-derived was prepared. Specifically, genes encoding signal sequences (N. Whittle, et al., Protein Eng., Vol. 1, p. 499, 1987) were connected to the 5' side of the heavy chain variable region genes of each BDC3-12A2, BDC3-12F5, and BDC13-32E3 and the constant region gene of human Igγ1 (consisting of the base sequence of base numbers 361 to 1353 of SEQ ID NO: 1) were connected to the 3' side thereof, and then the heavy chain genes were inserted to pEE6.4. Further, genes encoding signal sequences (N. Whittle, et al., mentioned above) were connected to the 5' side of the light chain variable region genes of the antibody and the constant region genes of human Igκ (consisting of the base sequence of base numbers 328 to 648 of SEQ ID NO: 3) were connected to the 3' side thereof, and then the light chain genes were inserted into pEE12.4.

The heavy chain gene sequence of each antibody inserted to pEE6.4 and the light chain gene sequence of each antibody inserted to pEE12.4 were analyzed using a sequencer, and from the amino acid sequence obtained as a result, the CDR sequence was determined with reference to Kabat database ("Sequences of Proteins of Immunological Interest", US Department of Health and Human Services, US Government Printing Office).

The base sequence of the heavy chain of the fully human antibody (fully human BDC3-12A2) of the prepared BDC3-12A2 is shown by SEQ ID NO: 1, the amino acid sequence encoded by the base sequence is shown by SEQ ID NO: 2, the base sequence of the light chain of the antibody is shown by SEQ ID NO: 3, and the amino acid sequence encoded by the base sequence is shown by SEQ ID NO: 4. The heavy chain variable region shown by SEQ ID NO: 2 consists of the amino acid sequence of the amino acid numbers 1 to 120 of SEQ ID NO: 2, and the CDR1, CDR2, and CDR3 of the heavy chain each consist of the amino acid sequence of the amino acid numbers 31 to 35, 50 to 66, and 99 to 109 of SEQ ID NO: 2. The variable region of the light chain shown by SEQ ID NO: 4 consists of the amino acid sequence of the amino acid numbers 1 to 109 of SEQ ID NO: 4, and the CDR1, CDR2, and CDR3 of the light chain each consist of the amino acid sequence of the amino acid numbers 24 to 34, 50 to 56, and 89 to 98 of SEQ ID NO: 4.

The base sequence of the heavy chain of the fully human antibody (fully human BDC3-12F5) of the prepared BDC3-12F5 is shown by SEQ ID NO: 5, the amino acid sequence encoded by the base sequence is shown by SEQ ID NO: 6, the base sequence of the light chain of the antibody is shown by SEQ ID NO: 7, and the amino acid sequence encoded by the base sequence is shown by SEQ ID NO: 8. The heavy chain variable region shown by SEQ ID NO: 6 consists of the amino acid sequence of the amino acid numbers 1 to 120 of SEQ ID NO: 6, and the CDR1, CDR2, and CDR3 of the heavy chain each consist of the amino acid sequence of the amino acid numbers 31 to 35, 50 to 66, and 99 to 109 of SEQ ID NO: 6. The variable region of the light chain shown by SEQ ID NO: 8 consists of the amino acid sequence of the amino acid numbers 1 to 108 of SEQ ID NO: 8, and the CDR1, CDR2, and CDR3 of the light chain each consist of the amino acid sequence of the amino acid numbers 24 to 34, 50 to 56, and 89 to 97 of SEQ ID NO: 8.

The base sequence of the heavy chain of the fully human antibody (fully human BDC13-32E3) of the prepared BDC13-32E3 is shown by SEQ ID NO: 9, the amino acid sequence encoded by the base sequence is shown by SEQ ID NO: 10, the base sequence of the light chain of the antibody is shown by SEQ ID NO: 11, and the amino acid sequence encoded by the base sequence is shown by SEQ ID NO: 12. The heavy chain variable region shown by SEQ ID NO: 10 consists of the amino acid sequence of the amino acid numbers 1 to 122 of SEQ ID NO: 10, and the CDR1, CDR2, and CDR3 of the heavy chain each consist of the amino acid sequence of the amino acid numbers 31 to 37, 52 to 67, and 100 to 111 of SEQ ID NO: 10. The variable region of the light chain shown by SEQ ID NO: 12 consists of the amino acid sequence of the amino acid numbers 1 to 108 of SEQ ID NO: 12, and the CDR1, CDR2, and CDR3 of the light chain each consist of the amino acid sequence of the amino acid numbers 24 to 34, 50 to 56, and 89 to 97 of SEQ ID NO: 12.

In order to prepare each fully human antibody, with reference to the method described in the protocol of a GS Gene Expression System (Lonza, Inc.), the above-described GS vector into which the genes of the heavy chain and the light chain of each antibody were respectively inserted was cleaved with a restriction enzyme by NotI and PvuI, and ligation was performed using a Ligation-Convenience Kit (NIPPONGENE, Inc.), thereby constructing a Double-Gene vector into which both genes of the heavy chain and the light chain were inserted. Next, the above-described Double-Gene vector was transfected to the CHOK1SV cells (Lonza, Inc.) by an electroporation method, and cultured in a CD-CHO Medium (Life Technologies, Inc.) to which methionine sulfoximine (SIGMA Corporation) had been added to a final concentration of 50 μM, for 5 days to 6 days. Each of the fully human antibodies was purified with Protein A column or Protein G column (GE Healthcare Japan Corporation) from the obtained culture supernatants.

Example 6

Analysis of the Amino Acid Modifications of Fully Human Antibody

As a result of analyzing the amino acid modifications of each of the fully human anti-human BDCA-2 antibodies purified in Example 5, it was found that pyroglutamylation at the N terminal of the heavy chain and deletion of lysine at the C terminal of the heavy chain occurred in the fully human BDC3-12A2; deletion of lysine at the C terminal of the heavy chain occurred in the fully human BDC3-12F5; and pyroglutamylation at the N terminal of the heavy chain and deletion of lysine at the C terminal of the heavy chain occurred in the fully human BDC13-32E3, in most of the purified antibodies.

Example 7

Evaluation of Binding Activity of Fully Human Antibody with Respect to Extracellular Region of Human BDCA-2

According to the method of Example 3, for a fully human antibody, the binding activity of the antibody against an extracellular region of human BDCA-2 was evaluated. However, the fully human antibodies (the fully human BDC3-12A2, the fully human BDC3-12F5, or the fully human BDC13-32E3) prepared in Example 5 were added, respectively, instead of the hybridoma-derived antibody. Further, an HRP-labeled rabbit anti-human IgG antibody (DAKO) was used, instead of the HRP-labeled rabbit anti-mouse IgG antibody. This activity evaluation test was carried out independently three times.

As a result, it was confirmed that all of the fully human antibodies of the present invention had high binding activity against the extracellular region of human BDCA-2 (Table 3). The EC50 values shown in Table 3 are an average of the EC50 values obtained from the three independent activity evaluations.

TABLE 3

Binding Activity of Fully Human Anti-Human BDCA-2 Antibody against Extracellular Region of Human BDCA-2

|  | EC50 (ng/mL) |
| --- | --- |
| Fully human BDC3-12A2 | 80 |
| Fully human BDC3-12F5 | 88 |
| Fully human BDC13-32E3 | 203 |

Example 8

Evaluation of Inhibitory Activity of Fully Human Antibody on Human IFNα Production According to the method of Example 4, for each fully human antibody prepared in Example 5, the function control activity of the antibody on pDCs was evaluated by using the production inhibition of IFNα produced from pDCs by the anti-human BDCA-2 antibody as an index. However, in this Example, in order to obtain more stable evaluation results, the cells were suspended at $5\times10^6$ cells/mL in an RPMI1640 culture medium containing human IL-3 and used for evaluation, using a lot having relatively much IFNα production with respect to ODN2216 stimuli among lots with a plurality of human peripheral blood mononuclear cells. In addition, each of the fully human antibodies (the fully human BDC3-12A2, the fully human BDC3-12F5, or the fully human BDC13-32E3) which had been diluted in 9 steps in a range from 1200 ng/mL to 0.06 ng/mL was added thereto, instead of the hybridoma-derived antibody. In this Example, AC144 was used as the comparative antibody. Further, this activity evaluation test was carried out independently twice.

As a result, it became clear that all of the fully human antibodies of the present invention had higher inhibitory activities on pDCs in both of the IC50 value and the IC90 value than the comparative antibody AC144 (Table 4). In addition, it became clear that the concentration of BDC3-12A2, BDC3-12F5, and BDC13-32E3 was lower than that of the comparative AC144 for complete inhibition of IFNα production from the IC90 value.

TABLE 4

Inhibitory Activity of Fully Human Anti-Human BDCA-2 Antibody on Human IFNα Production

|  | IC50 (ng/mL) | | IC90 (ng/mL) | |
| --- | --- | --- | --- | --- |
|  | First time | Second time | First time | Second time |
| Fully human BDC3-12A2 | 0.35 | 0.68 | 1.94 | 1.76 |
| Fully human BDC3-12F5 | 0.54 | 0.24 | 1.19 | 1.98 |
| Fully human BDC13-32E3 | 0.32 | 0.59 | 2.03 | 1.25 |
| AC144 | 2.12 | 3.83 | 20.6 | 26.8 |

INDUSTRIAL APPLICABILITY

The anti-human BDCA-2 antibody of the present invention is useful for preventing and treating autoimmune diseases in which pDCs specifically expressing human BDCA-2 are involved in disease pathology. Further, the polynucleotide, the expression vectors, the transformed host cell, and the methods for producing the antibody of the present invention are useful for producing the anti-human BDCA-2 antibody.

[Sequence List Free Text]

In the number heading <223> of the sequence list, description of "Artificial Sequence" is made. Specifically, the base sequences shown by SEQ ID NOS: 1 and 3 of the sequence list are the base sequences of the heavy chain and the light chain of the fully human BDC3-12A2, respectively, and the amino acid sequences shown by SEQ ID NOS: 2 and 4 are the amino acid sequences of the heavy chain and the light chain encoded by the SEQ ID NOS: 1 and 3, respectively. The base sequences shown by SEQ ID NOS: 5 and 7 of the sequence list are the base sequences of the heavy chain and the light chain of the fully human BDC3-12F5, respectively, and the amino acid sequences shown by SEQ ID NOS: 6 and 8 are the amino acid sequences of the heavy chain and the light chain encoded by the SEQ ID NOS: 5 and 7, respectively. The base sequences shown by SEQ ID NOS: 9 and 11 of the sequence list are the base sequences of the heavy chain and the light chain of the fully human BDC13-32E3, respectively, and the amino acid sequences shown by SEQ ID NOS: 10 and 12 are the amino acid sequences of the heavy chain and the light chain encoded by the SEQ ID NOS: 9 and 11, respectively. The base sequence shown by SEQ ID NO: 14 of the sequence list is the base sequence of the human BDCA-2 variant, and the amino acid sequence shown by SEQ ID NO: 15 is the amino acid sequence of the human BDCA-2 variant.

The invention claimed is:

1. A polynucleotide selected from the group consisting of the following (1) and (2):
   (1) polynucleotide comprising a base sequence encoding the heavy chain of an anti-human BDCA-2 antibody; and
   (2) polynucleotide comprising a base sequence encoding the light chain of the anti-human BDCA-2 antibody, wherein the anti-human BDCA-2 antibody of (1) and (2) is selected from any one of the following (a) to (c):
   (a) an anti-human BDCA-2 antibody comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4;
   (b) an anti-human BDCA-2 antibody comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8; and
   (c) an anti-human BDCA-2 antibody comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

2. An expression vector comprising the following (1) and/or (2);
   (1) polynucleotide comprising a base sequence encoding the heavy chain of an anti-human BDCA-2 antibody; and/or
   (2) polynucleotide comprising a base sequence encoding the light chain of the anti-human BDCA-2 antibody, wherein the anti-human BDCA-2 antibody of (1) and (2) is selected from any one of the following (a) to (c):
   (a) an anti-human BDCA-2 antibody comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4;
   (b) an anti-human BDCA-2 antibody comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8; and
   (c) an anti-human BDCA-2 antibody comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

3. A host cell selected from the group consisting of the following (a) to (d):
   (a) a host cell transformed with an expression vector comprising a polynucleotide comprising a base sequence encoding the heavy chain variable region of an anti-human BDCA-2 antibody or an antigen-binding fragment thereof and a polynucleotide comprising a base sequence encoding the light chain variable region of the anti-human BDCA-2 antibody or the antigen-binding fragment thereof;
   (b) a host cell transformed with an expression vector comprising a polynucleotide comprising a base sequence encoding the heavy chain variable region of an anti-human BDCA-2 antibody or an antigen-binding fragment thereof and an expression vector comprising a polynucleotide comprising a base sequence encoding the light chain variable region of the anti-human BDCA-2 antibody or the antigen-binding fragment thereof;
   (c) a host cell transformed with an expression vector comprising a polynucleotide comprising a base sequence encoding the heavy chain variable region of an anti-human BDCA-2 antibody or an antigen-binding fragment thereof; and
   (d) a host cell transformed with an expression vector comprising a polynucleotide comprising a base sequence encoding the light chain variable region of an anti-human BDCA-2 antibody or an antigen-binding fragment thereof,
   wherein the anti-human BDCA-2 antibody or the antigen-binding fragment thereof of (a)-(d) is selected from any one of the following (1) to (3):
   (1) an anti-human BDCA-2 antibody or an antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4;
   (2) an anti-human BDCA-2 antibody or an antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8; and
   (3) an anti-human BDCA-2 antibody or an antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12.

4. A host cell selected from the group consisting of following (a) to (d):
   (a) a host cell transformed with an expression vector comprising a polynucleotide comprising a base sequence encoding the heavy chain of an anti-human BDCA-2 antibody and a polynucleotide comprising a base sequence encoding the light chain of the anti-human BDCA-2 antibody;
   (b) a host cell transformed with an expression vector comprising a polynucleotide comprising a base sequence encoding the heavy chain of an anti-human BDCA-2 antibody and an expression vector comprising a polynucleotide comprising a base sequence encoding the light chain of the anti-human BDCA-2 antibody;
   (c) a host cell transformed with an expression vector comprising a polynucleotide comprising a base sequence encoding the heavy chain of an anti-human BDCA-2 antibody; and
   (d) a host cell transformed with an expression vector comprising a polynucleotide comprising a base sequence encoding the light chain of an anti-human BDCA-2 antibody,
   wherein the anti-human BDCA-2 antibody of (a)-(d) is selected from any one of the following (1) to (3):
   (1) an anti-human BDCA-2 antibody comprising a heavy chain consisting of the amino acid sequence shown by SEQ ID NO: 2 and a light chain consisting of the amino acid sequence shown by SEQ ID NO: 4;
   (2) an anti-human BDCA-2 antibody comprising a heavy chain consisting of the amino acid sequence shown by SEQ ID NO: 6 and a light chain consisting of the amino acid sequence shown by SEQ ID NO: 8; and
   (3) an anti-human BDCA-2 antibody comprising a heavy chain consisting of the amino acid sequence shown by SEQ ID NO: 10 and a light chain consisting of the amino acid sequence shown by SEQ ID NO: 12.

5. A method for producing an anti-human BDCA-2 antibody or an antigen-binding fragment thereof, comprising culturing host cell(s) selected from the group consisting of following (a) to (c) to express the anti-human BDCA-2 antibody or the antigen-binding fragment thereof:
   (a) a host cell transformed with an expression vector comprising a polynucleotide comprising a base sequence encoding the heavy chain variable region of an anti-human BDCA-2 antibody or an antigen-binding fragment thereof and a polynucleotide comprising a base sequence encoding the light chain variable region of the anti-human BDCA-2 antibody or the antigen-binding fragment thereof;
   (b) a host cell transformed with an expression vector comprising a polynucleotide comprising a base sequence encoding the heavy chain variable region of an anti-human BDCA-2 antibody or an antigen-binding fragment thereof and an expression vector comprising a polynucleotide comprising a base sequence encoding the light chain variable region of the anti-human BDCA-2 antibody or the antigen-binding fragment thereof; and
   (c) a host cell transformed with an expression vector comprising a polynucleotide comprising a base sequence encoding the heavy chain variable region of an anti-human BDCA-2 antibody or an antigen-binding fragment thereof and a host cell transformed with an expression vector comprising a polynucleotide comprising a base sequence encoding the light chain variable region of the anti-human BDCA-2 antibody or the antigen-binding fragment thereof,
   wherein the anti-human BDCA-2 antibody or the antigen-binding fragment thereof of (a)-(c) is selected from any one of the following (1) to (5):
   (1) an anti-human BDCA-2 antibody or an antigen-binding fragment thereof, comprising a heavy chain variable region consisting of the amino acid sequence of amino acid numbers 1 to 120 of SEQ ID NO: 2 and a light chain variable region consisting of the amino acid sequence of amino acid numbers 1 to 109 of SEQ ID NO: 4;

(2) an anti-human BDCA-2 antibody or an antigen-binding fragment thereof, comprising a heavy chain variable region consisting of the amino acid sequence of amino acid numbers 1 to 120 of SEQ ID NO: 6 and a light chain variable region consisting of the amino acid sequence of amino acid numbers 1 to 108 of SEQ ID NO: 8;

(3) an anti-human BDCA-2 antibody or an antigen-binding fragment thereof, comprising a heavy chain variable region consisting of the amino acid sequence of amino acid numbers 1 to 122 of SEQ ID NO: 10 and a light chain variable region consisting of the amino acid sequence of amino acid numbers 1 to 108 of SEQ ID NO: 12;

(4) an anti-human BDCA-2 antibody or an antigen-binding fragment thereof, comprising a heavy chain variable region consisting of the amino acid sequence of amino acid numbers 1 to 120 of SEQ ID NO: 2 in which glutamine of the amino acid number 1 is modified to pyroglutamic acid and a light chain variable region consisting of the amino acid sequence of amino acid numbers 1 to 109 of SEQ ID NO: 4; and (5) an anti-human BDCA-2 antibody or an antigen-binding fragment thereof, comprising a heavy chain variable region consisting of the amino acid sequence of amino acid numbers 1 to 122 of SEQ ID NO: 10 in which glutamine of the amino acid number 1 is modified to pyroglutamic acid and a light chain variable region consisting of the amino acid sequence of amino acid numbers 1 to 108 of SEQ ID NO: 12.

6. A method for producing an anti-human BDCA-2 antibody, comprising culturing host cell(s) selected from the group consisting of following (a) to (c) to express the anti-human BDCA-2 antibody:

(a) a host cell transformed with an expression vector comprising a polynucleotide comprising a base sequence encoding the heavy chain of an anti-human BDCA-2 antibody and a polynucleotide comprising a base sequence encoding the light chain of the anti-human BDCA-2 antibody;

(b) a host cell transformed with an expression vector comprising a polynucleotide comprising a base sequence encoding the heavy chain of an anti-human BDCA-2 antibody and an expression vector comprising a polynucleotide comprising a base sequence encoding the light chain of the anti-human BDCA-2 antibody; and (c) a host cell transformed with an expression vector comprising a polynucleotide comprising a base sequence encoding the heavy chain of an anti-human BDCA-2 antibody and a host cell transformed with an expression vector comprising a polynucleotide comprising a base sequence encoding the light chain of the anti-human BDCA-2 antibody, wherein the anti-human BDCA-2 antibody of (a)-(c) is selected from any one of the following (1) to (3):

(1) an anti-human BDCA-2 antibody comprising a heavy chain consisting of the amino acid sequence shown by SEQ ID NO: 2 and a light chain consisting of the amino acid sequence shown by SEQ ID NO: 4;

(2) an anti-human BDCA-2 antibody comprising a heavy chain consisting of the amino acid sequence shown by SEQ ID NO: 6 and a light chain consisting of the amino acid sequence shown by SEQ ID NO: 8; and (3) an anti-human BDCA-2 antibody comprising a heavy chain consisting of the amino acid sequence shown by SEQ ID NO: 10 and a light chain consisting of the amino acid sequence shown by SEQ ID NO: 12.

* * * * *

SEQUENCE LISTING

<160> NUMBER OF SEQ ID NOS: 16

<210> SEQ ID NO 1
<211> LENGTH: 1353
<212> TYPE: DNA
<213> ORGANISM: Artificial Sequence
<220> FEATURE:
<223> OTHER INFORMATION: H-chain of anti-human BDCA-2 antibody
<220> FEATURE:
<221> NAME/KEY: CDS
<222> LOCATION: (1)..(1353)

<400> SEQUENCE: 1

```
cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gca gcg tct gga ttc acc ttg agt agc tat      96
Ser Leu Arg Leu Ser Cys Ala Ala Ser Gly Phe Thr Leu Ser Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tgg tat gat gga aat gat aaa tac tat gca gac tcc gtg     192
Ala Val Ile Trp Tyr Asp Gly Asn Asp Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa gtg aac agc ctg aga gcc gag gac acg gct gtg tat tac tgt     288
Leu Gln Val Asn Ser Leu Arg Ala Glu Asp Thr Ala Val Tyr Tyr Cys
                85                  90                  95 gcg aga gga act gga act cct tac tgg tac ttc gat ctc tgg ggc cgt     336
Ala Arg Gly Thr Gly Thr Pro Tyr Trp Tyr Phe Asp Leu Trp Gly Arg
            100                 105                 110 ggc acc ctg gtc act gtc tcc tca gcc tcc acc aag ggc cca tcg gtc     384
Gly Thr Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc     432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg     480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc     528
Trp Asn Ser Gly Ala Leu Thr Ser Gly Val His Thr Phe Pro Ala Val
                165                 170                 175 cta cag tcc tca gga ctc tac tcc ctt agt agc gtg gtg acc gtg ccc     576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag     624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt gac     672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga     720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc     768
Pro Ser Val Phe Leu Phe Pro Pro Lys Pro Lys Asp Thr Leu Met Ile
                245                 250                 255
```

| | | | | | | | | | | | | | | | | |
|---|---|---|---|---|---|---|---|---|---|---|---|---|---|---|---|---|
| tcc | cgg | acc | cct | gag | gtc | aca | tgc | gtg | gtg | gtg | gac | gtg | agc | cac | gaa | 816 |
| Ser | Arg | Thr | Pro | Glu | Val | Thr | Cys | Val | Val | Val | Asp | Val | Ser | His | Glu | |
| | | | 260 | | | | 265 | | | | 270 | | | | | |
| gac | cct | gag | gtc | aag | ttc | aac | tgg | tac | gtg | gac | ggc | gtg | gag | gtg | cat | 864 |
| Asp | Pro | Glu | Val | Lys | Phe | Asn | Trp | Tyr | Val | Asp | Gly | Val | Glu | Val | His | |
| | | 275 | | | | | 280 | | | | 285 | | | | | |
| aat | gcc | aag | aca | aag | ccg | cgg | gag | gag | cag | tac | aac | agc | acg | tac | cgt | 912 |
| Asn | Ala | Lys | Thr | Lys | Pro | Arg | Glu | Glu | Gln | Tyr | Asn | Ser | Thr | Tyr | Arg | |
| | | 290 | | | | 295 | | | | | 300 | | | | | |
| gtg | gtc | agc | gtc | ctc | acc | gtc | ctg | cac | cag | gac | tgg | ctg | aat | ggc | aag | 960 |
| Val | Val | Ser | Val | Leu | Thr | Val | Leu | His | Gln | Asp | Trp | Leu | Asn | Gly | Lys | |
| 305 | | | | | 310 | | | | | 315 | | | | | 320 | |
| gag | tac | aag | tgc | aag | gtc | tcc | aac | aaa | gcc | ctc | cca | gcc | ccc | atc | gag | 1008 |
| Glu | Tyr | Lys | Cys | Lys | Val | Ser | Asn | Lys | Ala | Leu | Pro | Ala | Pro | Ile | Glu | |
| | | | | 325 | | | | | 330 | | | | | 335 | | |
| aaa | acc | atc | tcc | aaa | gcc | aaa | ggg | cag | ccc | cga | gaa | cca | cag | gtg | tac | 1056 |
| Lys | Thr | Ile | Ser | Lys | Ala | Lys | Gly | Gln | Pro | Arg | Glu | Pro | Gln | Val | Tyr | |
| | | | 340 | | | | | 345 | | | | | 350 | | | |
| acc | ctg | ccc | cca | tcc | cgg | gat | gag | ctg | acc | aag | aac | cag | gtc | agc | ctg | 1104 |
| Thr | Leu | Pro | Pro | Ser | Arg | Asp | Glu | Leu | Thr | Lys | Asn | Gln | Val | Ser | Leu | |
| | | | 355 | | | | | 360 | | | | | 365 | | | |
| acc | tgc | ctg | gtc | aaa | ggc | ttc | tat | ccc | agc | gac | atc | gcc | gtg | gag | tgg | 1152 |
| Thr | Cys | Leu | Val | Lys | Gly | Phe | Tyr | Pro | Ser | Asp | Ile | Ala | Val | Glu | Trp | |
| 370 | | | | | 375 | | | | | 380 | | | | | | |
| gag | agc | aat | ggg | cag | ccg | gag | aac | aac | tac | aag | acc | acg | cct | ccc | gtg | 1200 |
| Glu | Ser | Asn | Gly | Gln | Pro | Glu | Asn | Asn | Tyr | Lys | Thr | Thr | Pro | Pro | Val | |
| 385 | | | | 390 | | | | | 395 | | | | | 400 | | |
| ctg | gac | tcc | gac | ggc | tcc | ttc | ttc | ctc | tac | agc | aag | ctc | acc | gtg | gac | 1248 |
| Leu | Asp | Ser | Asp | Gly | Ser | Phe | Phe | Leu | Tyr | Ser | Lys | Leu | Thr | Val | Asp | |
| | | | | 405 | | | | | 410 | | | | | 415 | | |
| aag | agc | agg | tgg | cag | cag | ggg | aac | gtc | ttc | tca | tgc | tcc | gtg | atg | cat | 1296 |
| Lys | Ser | Arg | Trp | Gln | Gln | Gly | Asn | Val | Phe | Ser | Cys | Ser | Val | Met | His | |
| | | | 420 | | | | | 425 | | | | | 430 | | | |
| gag | gct | ctg | cac | aac | cac | tac | acg | cag | aag | agc | ctc | tcc | ctg | tct | ccg | 1344 |
| Glu | Ala | Leu | His | Asn | His | Tyr | Thr | Gln | Lys | Ser | Leu | Ser | Leu | Ser | Pro | |
| | | | 435 | | | | | 440 | | | | | 445 | | | |
| ggt | aaa | tga | | | | | | | | | | | | | | 1353 |
| Gly | Lys | | | | | | | | | | | | | | | |
| | 450 | | | | | | | | | | | | | | | |

```
<210> SEQ ID NO 2
<211> LENGTH: 450
<212> TYPE: PRT
<213> ORGANISM: Artificial Sequence
<220> FEATURE:
<223> OTHER INFORMATION: Synthetic Construct

<400> SEQUENCE: 2
```

Gln Val Gln Leu Val Glu Ser Gly Gly Gly Val Val Gln Pro Gly Arg
1               5                  10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Gly Thr Gly Thr Pro Tyr Trp Tyr Phe Asp Leu Trp Gly Arg
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 648
<212> TYPE: DNA
<213> ORGANISM: Artificial Sequence
<220> FEATURE:
<223> OTHER INFORMATION: L-chain of anti-human BDCA-2 antibody
<220> FEATURE:
<221> NAME/KEY: CDS

<222> LOCATION: (1)..(648)

<400> SEQUENCE: 3

```
gaa att gtg ttg aca cag tct cca gcc acc ctg tct ttg tct cca ggg        48
Glu Ile Val Leu Thr Gln Ser Pro Ala Thr Leu Ser Leu Ser Pro Gly
1               5                   10                  15 gaa aga gcc acc ctc tcc tgc agg gcc agt cag agt gtt aac aac tac        96
Glu Arg Ala Thr Leu Ser Cys Arg Ala Ser Gln Ser Val Asn Asn Tyr
            20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc       192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc acc tgg cct ccg       288
Glu Asp Phe Ala Val Tyr Tyr Cys Gln Gln Arg Ser Thr Trp Pro Pro
                85                  90                  95 tac act ttt ggc cag ggg acc aag ctg gag atc aaa cgg act gtg gct       336
Tyr Thr Phe Gly Gln Gly Thr Lys Leu Glu Ile Lys Arg Thr Val Ala
            100                 105                 110 gca cca tct gtc ttc atc ttc ccg cca tct gat gag cag ttg aaa tct       384
Ala Pro Ser Val Phe Ile Phe Pro Pro Ser Asp Glu Gln Leu Lys Ser
        115                 120                 125 gga act gcc tct gtt gtg tgc ctg ctg aat aac ttc tat ccc aga gag       432
Gly Thr Ala Ser Val Val Cys Leu Leu Asn Asn Phe Tyr Pro Arg Glu
    130                 135                 140 gcc aaa gta cag tgg aag gtg gat aac gcc ctc caa tcg ggt aac tcc       480
Ala Lys Val Gln Trp Lys Val Asp Asn Ala Leu Gln Ser Gly Asn Ser
145                 150                 155                 160 cag gag agt gtc aca gag cag gac agc aag gac agc acc tac agc ctc       528
Gln Glu Ser Val Thr Glu Gln Asp Ser Lys Asp Ser Thr Tyr Ser Leu
                165                 170                 175 agc agc acc ctg acg ctg agc aaa gca gac tac gag aaa cac aaa gtc       576
Ser Ser Thr Leu Thr Leu Ser Lys Ala Asp Tyr Glu Lys His Lys Val
            180                 185                 190 tac gcc tgc gaa gtc acc cat cag ggc ctg agc tcg ccc gtc aca aag       624
Tyr Ala Cys Glu Val Thr His Gln Gly Leu Ser Ser Pro Val Thr Lys
        195                 200                 205 agc ttc aac agg gga gag tgt tag                                       648
Ser Phe Asn Arg Gly Glu Cys
    210                 215
```

<210> SEQ ID NO 4
<211> LENGTH: 215
<212> TYPE: PRT
<213> ORGANISM: Artificial Sequence
<220> FEATURE:
<223> OTHER INFORMATION: Synthetic Construct

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Tyr
            20                  25                  30

Leu Ala Trp Tyr Gln Gln Lys Pro Gly Gln Ala Pro Arg Leu Leu Ile
        35                  40                  45
```

-continued

```
Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Thr Trp Pro Pro
                 85                  90                  95

Tyr Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 5
<211> LENGTH: 1353
<212> TYPE: DNA
<213> ORGANISM: Artificial Sequence
<220> FEATURE:
<223> OTHER INFORMATION: H-chain of anti-human BDCA-2 antibody
<220> FEATURE:
<221> NAME/KEY: CDS
<222> LOCATION: (1)..(1353)

<400> SEQUENCE: 5 gag gtg cag ctg gtg gag tct ggg gga ggc ttg gtc cag ccg ggg ggg      48
Glu Val Gln Leu Val Glu Ser Gly Gly Gly Leu Val Gln Pro Gly Gly
  1               5                  10                  15 tcc ctg aga ctc tcc tgt gca gcc tct gga ttc acc ttt agt aat tat      96
Ser Leu Arg Leu Ser Cys Ala Ala Ser Gly Phe Thr Phe Ser Asn Tyr
             20                  25                  30 ttg atg aac tgg gtc cgc cag gct cca ggg aag ggg ctg gag tgg gtg     144
Leu Met Asn Trp Val Arg Gln Ala Pro Gly Lys Gly Leu Glu Trp Val
         35                  40                  45 gcc aac ata gaa caa gat gga agt gag aaa tac tat gtg gac tct gtg     192
Ala Asn Ile Glu Gln Asp Gly Ser Glu Lys Tyr Tyr Val Asp Ser Val
     50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
 65                  70                  75                  80 cta caa atg aac agc ctg aga gcc gag gac acg gct gtg tat ttc tgt     288
Leu Gln Met Asn Ser Leu Arg Ala Glu Asp Thr Ala Val Tyr Phe Cys
                 85                  90                  95 gcg aga gat gga gat aca gct atg att act ttt gac ttc tgg ggc cag     336
Ala Arg Asp Gly Asp Thr Ala Met Ile Thr Phe Asp Phe Trp Gly Gln
                100                 105                 110 gga act ctg gtc acc gtc tcc tca gcc tcc acc aag ggc cca tcg gtc     384
Gly Thr Leu Val Thr Val Ser Ser Ala Ser Thr Lys Gly Pro Ser Val
            115                 120                 125 ttc ccc ctg gca ccc tcc tcc aag agc acc tct ggg ggc aca gcg gcc     432
```

```
                Phe Pro Leu Ala Pro Ser Ser Lys Ser Thr Ser Gly Gly Thr Ala Ala
                    130                 135                 140 ctg ggc tgc ctg gtc aag gac tac ttc ccc gaa ccg gtg acg gtg tcg        480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc        528
Trp Asn Ser Gly Ala Leu Thr Ser Gly Val His Thr Phe Pro Ala Val
                165                 170                 175 cta cag tcc tca gga ctc tac tcc ctt agt agc gtg gtg acc gtg ccc        576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag        624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt gac        672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga        720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc        768
Pro Ser Val Phe Leu Phe Pro Pro Lys Pro Lys Asp Thr Leu Met Ile
                245                 250                 255 tcc cgg acc cct gag gtc aca tgc gtg gtg gtg gac gtg agc cac gaa        816
Ser Arg Thr Pro Glu Val Thr Cys Val Val Val Asp Val Ser His Glu
            260                 265                 270 gac cct gag gtc aag ttc aac tgg tac gtg gac ggc gtg gag gtg cat        864
Asp Pro Glu Val Lys Phe Asn Trp Tyr Val Asp Gly Val Glu Val His
        275                 280                 285 aat gcc aag aca aag ccg cgg gag gag cag tac aac agc acg tac cgt        912
Asn Ala Lys Thr Lys Pro Arg Glu Glu Gln Tyr Asn Ser Thr Tyr Arg
    290                 295                 300 gtg gtc agc gtc ctc acc gtc ctg cac cag gac tgg ctg aat ggc aag        960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag       1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac       1056
Lys Thr Ile Ser Lys Ala Lys Gly Gln Pro Arg Glu Pro Gln Val Tyr
            340                 345                 350 acc ctg ccc cca tcc cgg gat gag ctg acc aag aac cag gtc agc ctg       1104
Thr Leu Pro Pro Ser Arg Asp Glu Leu Thr Lys Asn Gln Val Ser Leu
        355                 360                 365 acc tgc ctg gtc aaa ggc ttc tat ccc agc gac atc gcc gtg gag tgg       1152
Thr Cys Leu Val Lys Gly Phe Tyr Pro Ser Asp Ile Ala Val Glu Trp
    370                 375                 380 gag agc aat ggg cag ccg gag aac aac tac aag acc acg cct ccc gtg       1200
Glu Ser Asn Gly Gln Pro Glu Asn Asn Tyr Lys Thr Thr Pro Pro Val
385                 390                 395                 400 ctg gac tcc gac ggc tcc ttc ttc ctc tac agc aag ctc acc gtg gac       1248
Leu Asp Ser Asp Gly Ser Phe Phe Leu Tyr Ser Lys Leu Thr Val Asp
                405                 410                 415 aag agc agg tgg cag cag ggg aac gtc ttc tca tgc tcc gtg atg cat       1296
Lys Ser Arg Trp Gln Gln Gly Asn Val Phe Ser Cys Ser Val Met His
            420                 425                 430 gag gct ctg cac aac cac tac acg cag aag agc ctc tcc ctg tct ccg       1344
Glu Ala Leu His Asn His Tyr Thr Gln Lys Ser Leu Ser Leu Ser Pro
        435                 440                 445
```

```
ggt aaa tga                                                                1353
Gly Lys
    450

<210> SEQ ID NO 6
<211> LENGTH: 450
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Leu Met Asn Trp Val Arg Gln Ala Pro Gly Lys Gly Leu Glu Trp Val
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Asp Gly Asp Thr Ala Met Ile Thr Phe Asp Phe Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 7
<211> LENGTH: 645
<212> TYPE: DNA
<213> ORGANISM: Artificial Sequence
<220> FEATURE:
<223> OTHER INFORMATION: L-chain of anti-human BDCA-2 antibody
<220> FEATURE:
<221> NAME/KEY: CDS
<222> LOCATION: (1)..(645)

<400> SEQUENCE: 7
```

| | | | | | | | | | | | | | | | | |
|---|---|---|---|---|---|---|---|---|---|---|---|---|---|---|---|---|
| gac | atc | cag | atg | acc | cag | tct | cca | tct | tcc | gtg | tct | gca | tct | gta | gga | 48 |
| Asp | Ile | Gln | Met | Thr | Gln | Ser | Pro | Ser | Ser | Val | Ser | Ala | Ser | Val | Gly | |
| 1 | | | | 5 | | | | | 10 | | | | | 15 | | |

```
gac aga gtc acc atc act tgt cgg gcg agt cag ggc att agg aga tgg    96
Asp Arg Val Thr Ile Thr Cys Arg Ala Ser Gln Gly Ile Arg Arg Trp
            20                  25                  30 tta gcc tgg tat cag cag aaa cca ggg aaa gcc cct aag ctc ctg atc   144
Leu Ala Trp Tyr Gln Gln Lys Pro Gly Lys Ala Pro Lys Leu Leu Ile
        35                  40                  45 tat gct gca tcc agt ttg caa agg ggg gtc cca tca agg ttc agc ggc   192
Tyr Ala Ala Ser Ser Leu Gln Arg Gly Val Pro Ser Arg Phe Ser Gly
50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
65                  70                  75                  80 gaa gat ttt gca act tac tat tgt caa cag gct aac agt ttc ccg tgg   288
Glu Asp Phe Ala Thr Tyr Tyr Cys Gln Gln Ala Asn Ser Phe Pro Trp
                85                  90                  95 acg ttc ggc caa ggg acc aag gtg gaa atc aaa cgg act gtg gct gca   336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga   384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc   432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag   480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc   528
Glu Ser Val Thr Glu Gln Asp Ser Lys Asp Ser Thr Tyr Ser Leu Ser
                165                 170                 175
```

| | | |
|---|---|---|
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>180 185 190 | | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>195 200 205 | | 624 |
| ttc aac agg gga gag tgt tag<br>Phe Asn Arg Gly Glu Cys<br>210 | | 645 |

<210> SEQ ID NO 8
<211> LENGTH: 214
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 1359
<212> TYPE: DNA
<213> ORGANISM: Artificial Sequence
<220> FEATURE:
<223> OTHER INFORMATION: H-chain of anti-human BDCA-2 antibody
<220> FEATURE:
<221> NAME/KEY: CDS
<222> LOCATION: (1)..(1359)

<400> SEQUENCE: 9

| | | |
|---|---|---|
| cag gtg cag ctg cag gag tcg ggc cca gga ctg gtg aag cct tca cag<br>Gln Val Gln Leu Gln Glu Ser Gly Pro Gly Leu Val Lys Pro Ser Gln | | 48 |

-continued

```
1               5                   10                  15
acc ctg tcc ctc acc tgc act gtc tct ggt ggc tcc atc agc agt ggt        96
Thr Leu Ser Leu Thr Cys Thr Val Ser Gly Gly Ser Ile Ser Ser Gly
             20                  25                  30 ggt tac tac tgg aac tgg atc cgc cag cac cca ggg aag ggc ctg gag       144
Gly Tyr Tyr Trp Asn Trp Ile Arg Gln His Pro Gly Lys Gly Leu Glu
             35                  40                  45 tgg att ggg tac atc tat tat agt ggg aac acc tac tac aac ccg tcc       192
Trp Ile Gly Tyr Ile Tyr Tyr Ser Gly Asn Thr Tyr Tyr Asn Pro Ser
         50                  55                  60 ctc aag agt cga gtt acc att tca gtg gac acg tct aag aac cag ttc       240
Leu Lys Ser Arg Val Thr Ile Ser Val Asp Thr Ser Lys Asn Gln Phe
65                  70                  75                  80 tcc ctg aag ctg agc tct gtg act gcc gcg gac gcg gcc gtg tat cat       288
Ser Leu Lys Leu Ser Ser Val Thr Ala Ala Asp Ala Ala Val Tyr His
                 85                  90                  95 tgt gcg aga ggc tac ggt gac tac ggg ggg gga tat ttt gac tac tgg       336
Cys Ala Arg Gly Tyr Gly Asp Tyr Gly Gly Gly Tyr Phe Asp Tyr Trp
             100                 105                 110 ggc cag gga acc ctg gtc acc gtc tcc tca gcc tcc acc aag ggc cca       384
Gly Gln Gly Thr Leu Val Thr Val Ser Ser Ala Ser Thr Lys Gly Pro
             115                 120                 125 tcg gtc ttc ccc ctg gca ccc tcc tcc aag agc acc tct ggg ggc aca       432
Ser Val Phe Pro Leu Ala Pro Ser Ser Lys Ser Thr Ser Gly Gly Thr
     130                 135                 140 gcg gcc ctg ggc tgc ctg gtc aag gac tac ttc ccc gaa ccg gtg acg       480
Ala Ala Leu Gly Cys Leu Val Lys Asp Tyr Phe Pro Glu Pro Val Thr
145                 150                 155                 160 gtg tcg tgg aac tca ggc gcc ctg acc agc ggc gtg cac acc ttc ccg       528
Val Ser Trp Asn Ser Gly Ala Leu Thr Ser Gly Val His Thr Phe Pro
                 165                 170                 175 gct gtc cta cag tcc tca gga ctc tac tcc ctt agt agc gtg gtg acc       576
Ala Val Leu Gln Ser Ser Gly Leu Tyr Ser Leu Ser Ser Val Val Thr
             180                 185                 190 gtg ccc tcc agc agc ttg ggc acc cag acc tac atc tgc aac gtg aat       624
Val Pro Ser Ser Ser Leu Gly Thr Gln Thr Tyr Ile Cys Asn Val Asn
             195                 200                 205 cac aag ccc agc aac acc aag gtg gac aag aaa gtt gag ccc aaa tct       672
His Lys Pro Ser Asn Thr Lys Val Asp Lys Lys Val Glu Pro Lys Ser
         210                 215                 220 tgt gac aaa act cac aca tgc cca ccg tgc cca gca cct gaa ctc ctg       720
Cys Asp Lys Thr His Thr Cys Pro Pro Cys Pro Ala Pro Glu Leu Leu
225                 230                 235                 240 ggg gga ccg tca gtc ttc ctc ttc ccc cca aaa ccc aag gac acc ctc       768
Gly Gly Pro Ser Val Phe Leu Phe Pro Pro Lys Pro Lys Asp Thr Leu
                 245                 250                 255 atg atc tcc cgg acc cct gag gtc aca tgc gtg gtg gtg gac gtg agc       816
Met Ile Ser Arg Thr Pro Glu Val Thr Cys Val Val Val Asp Val Ser
             260                 265                 270 cac gaa gac cct gag gtc aag ttc aac tgg tac gtg gac ggc gtg gag       864
His Glu Asp Pro Glu Val Lys Phe Asn Trp Tyr Val Asp Gly Val Glu
             275                 280                 285 gtg cat aat gcc aag aca aag ccg cgg gag gag cag tac aac agc acg       912
Val His Asn Ala Lys Thr Lys Pro Arg Glu Glu Gln Tyr Asn Ser Thr
         290                 295                 300 tac cgt gtg gtc agc gtc ctc acc gtc ctg cac cag gac tgg ctg aat       960
Tyr Arg Val Val Ser Val Leu Thr Val Leu His Gln Asp Trp Leu Asn
305                 310                 315                 320 ggc aag gag tac aag tgc aag gtc tcc aac aaa gcc ctc cca gcc ccc      1008
```

```
Gly Lys Glu Tyr Lys Cys Lys Val Ser Asn Lys Ala Leu Pro Ala Pro
                325                 330                 335 atc gag aaa acc atc tcc aaa gcc aaa ggg cag ccc cga gaa cca cag      1056
Ile Glu Lys Thr Ile Ser Lys Ala Lys Gly Gln Pro Arg Glu Pro Gln
            340                 345                 350 gtg tac acc ctg ccc cca tcc cgg gat gag ctg acc aag aac cag gtc      1104
Val Tyr Thr Leu Pro Pro Ser Arg Asp Glu Leu Thr Lys Asn Gln Val
        355                 360                 365 agc ctg acc tgc ctg gtc aaa ggc ttc tat ccc agc gac atc gcc gtg      1152
Ser Leu Thr Cys Leu Val Lys Gly Phe Tyr Pro Ser Asp Ile Ala Val
    370                 375                 380 gag tgg gag agc aat ggg cag ccg gag aac aac tac aag acc acg cct      1200
Glu Trp Glu Ser Asn Gly Gln Pro Glu Asn Asn Tyr Lys Thr Thr Pro
385                 390                 395                 400 ccc gtg ctg gac tcc gac ggc tcc ttc ttc ctc tac agc aag ctc acc      1248
Pro Val Leu Asp Ser Asp Gly Ser Phe Phe Leu Tyr Ser Lys Leu Thr
                405                 410                 415 gtg gac aag agc agg tgg cag cag ggg aac gtc ttc tca tgc tcc gtg      1296
Val Asp Lys Ser Arg Trp Gln Gln Gly Asn Val Phe Ser Cys Ser Val
            420                 425                 430 atg cat gag gct ctg cac aac cac tac acg cag aag agc ctc tcc ctg      1344
Met His Glu Ala Leu His Asn His Tyr Thr Gln Lys Ser Leu Ser Leu
        435                 440                 445 tct ccg ggt aaa tga                                                  1359
Ser Pro Gly Lys
    450

<210> SEQ ID NO 10
<211> LENGTH: 452
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Ala Ala Val Tyr His
                85                  90                  95

Cys Ala Arg Gly Tyr Gly Asp Tyr Gly Gly Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
            180                 185                 190
Val Pro Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 11
<211> LENGTH: 645
<212> TYPE: DNA
<213> ORGANISM: Artificial Sequence
<220> FEATURE:
<223> OTHER INFORMATION: L-chain of anti-human BDCA-2 antibody
<220> FEATURE:
<221> NAME/KEY: CDS
<222> LOCATION: (1)..(645)

<400> SEQUENCE: 11 gac atc cag atg acc cag tct cca tcc tcc ctg tct gca tct gta gga    48
Asp Ile Gln Met Thr Gln Ser Pro Ser Ser Leu Ser Ala Ser Val Gly
1               5                   10                  15 gac aga gtc acc atc act tgc cag gcg agt cag gac att agc aac tat    96
Asp Arg Val Thr Ile Thr Cys Gln Ala Ser Gln Asp Ile Ser Asn Tyr
                20                  25                  30 tta aat tgg tat cag cag aaa cca ggg aaa gcc cct aag ttc ctg atc   144
Leu Asn Trp Tyr Gln Gln Lys Pro Gly Lys Ala Pro Lys Phe Leu Ile
            35                  40                  45 tac gat gta tcc aat ttg gaa aca ggg gtc cca tca agg ttc agt gga   192
```

```
Tyr Asp Val Ser Asn Leu Glu Thr Gly Val Pro Ser Arg Phe Ser Gly
     50                  55                  60 agt gga tct ggg aca gat ttt act ttc acc atc agc agc ctg cag cct     240
Ser Gly Ser Gly Thr Asp Phe Thr Phe Thr Ile Ser Ser Leu Gln Pro
 65                  70                  75                  80 gaa gat att gca aca tat tac tgt caa cag tat gat aat ctc ccg tac     288
Glu Asp Ile Ala Thr Tyr Tyr Cys Gln Gln Tyr Asp Asn Leu Pro Tyr
                 85                  90                  95 act ttt ggc cag ggg acc aag ctg gag atc aaa cgg act gtg gct gca     336
Thr Phe Gly Gln Gly Thr Lys Leu Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tgt tag                                         645
Phe Asn Arg Gly Glu Cys
    210

<210> SEQ ID NO 12
<211> LENGTH: 214
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Phe Leu Ile
         35                  40                  45

Tyr Asp Val Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 213
<212> TYPE: PRT
<213> ORGANISM: Homo sapiens

<400> SEQUENCE: 13

Met Val Pro Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
            20                  25                  30

Ser Val Cys Phe Thr Val Ser Ser Val Val Pro His Asn Phe Met Tyr
        35                  40                  45

Ser Lys Thr Val Lys Arg Leu Ser Lys Leu Arg Glu Tyr Gln Gln Tyr
    50                  55                  60

His Pro Ser Leu Thr Cys Val Met Glu Gly Lys Asp Ile Glu Asp Trp
65                  70                  75                  80

Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
            100                 105                 110

Val Met Gly Ala Asp Leu Val Val Ile Asn Thr Arg Glu Glu Gln Asp
        115                 120                 125

Phe Ile Ile Gln Asn Leu Lys Arg Asn Ser Ser Tyr Phe Leu Gly Leu
    130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
            180                 185                 190

Trp Asn Asp Ile His Cys His Val Pro Gln Lys Ser Ile Cys Lys Met
        195                 200                 205

Lys Lys Ile Tyr Ile
    210

<210> SEQ ID NO 14
<211> LENGTH: 642
<212> TYPE: DNA
<213> ORGANISM: Artificial Sequence
<220> FEATURE:
<223> OTHER INFORMATION: Human BDCA-2 mutant
<220> FEATURE:
<221> NAME/KEY: CDS
<222> LOCATION: (1)..(642)

<400> SEQUENCE: 14

```
atg gtg cct gaa gaa gag cct caa gac cga gag aaa gga ctc tgg tgg      48
Met Val Pro Glu Glu Glu Pro Gln Asp Arg Glu Lys Gly Leu Trp Trp
1               5                   10                  15 ttc cag ttg aag gtc tgg tcc atg gca gtc gta tcc atc ttg ctc ctc      96
Phe Gln Leu Lys Val Trp Ser Met Ala Val Val Ser Ile Leu Leu Leu
            20                  25                  30 tgt gtc tgt ttc act gtg agt tct gtg gtg cct cac aat ttt atg tat     144
Cys Val Cys Phe Thr Val Ser Ser Val Val Pro His Asn Phe Met Tyr
        35                  40                  45 agc aaa act gtc aag agg ctg tcc aag tta cga gag tat caa cag tat     192
Ser Lys Thr Val Lys Arg Leu Ser Lys Leu Arg Glu Tyr Gln Gln Tyr
    50                  55                  60 cat cca agc ctg acc tgc gtc atg gaa gga aag gac ata gaa gat tgg     240
His Pro Ser Leu Thr Cys Val Met Glu Gly Lys Asp Ile Glu Asp Trp
65                  70                  75                  80 agc tgc tgc cca acc cct tgg act tca ttt cag tct agt tgc tac ttt     288
Ser Cys Cys Pro Thr Pro Trp Thr Ser Phe Gln Ser Ser Cys Tyr Phe
                85                  90                  95 att tct act ggg atg caa tct tgg act aag agt caa aag aac tgt tct     336
Ile Ser Thr Gly Met Gln Ser Trp Thr Lys Ser Gln Lys Asn Cys Ser
            100                 105                 110 gtg atg ggg gct gat ctg gtg gtg atc aac acc agg gaa gaa cag gat     384
Val Met Gly Ala Asp Leu Val Val Ile Asn Thr Arg Glu Glu Gln Asp
        115                 120                 125 ttc atc att cag aat ctg aaa aga aat tct tct tat ttt ctg ggg ctg     432
Phe Ile Ile Gln Asn Leu Lys Arg Asn Ser Ser Tyr Phe Leu Gly Leu
    130                 135                 140 tca gat cca ggg ggt cgg cga cat tgg caa tgg gtt gac cag aca cca     480
Ser Asp Pro Gly Gly Arg Arg His Trp Gln Trp Val Asp Gln Thr Pro
145                 150                 155                 160 tac aat gaa aat gtc aca ttc tgg cac tca ggt gaa ccc aat aac ctt     528
Tyr Asn Glu Asn Val Thr Phe Trp His Ser Gly Glu Pro Asn Asn Leu
                165                 170                 175 gat gag cgt tgt gcg ata ata aat ttc cgt tct tca gaa gaa tgg ggc     576
Asp Glu Arg Cys Ala Ile Ile Asn Phe Arg Ser Ser Glu Glu Trp Gly
            180                 185                 190 tgg aat gac att cac tgt cat gta cct cag aag tca att tgc aag atg     624
Trp Asn Asp Ile His Cys His Val Pro Gln Lys Ser Ile Cys Lys Met
        195                 200                 205 aag aag atc tac ata taa                                              642
Lys Lys Ile Tyr Ile
    210
```

<210> SEQ ID NO 15
<211> LENGTH: 213
<212> TYPE: PRT
<213> ORGANISM: Artificial Sequence
<220> FEATURE:
<223> OTHER INFORMATION: Synthetic Construct

<400> SEQUENCE: 15

```
Met Val Pro Glu Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
            20                  25                  30

Cys Val Cys Phe Thr Val Ser Ser Val Val Pro His Asn Phe Met Tyr
        35                  40                  45

Ser Lys Thr Val Lys Arg Leu Ser Lys Leu Arg Glu Tyr Gln Gln Tyr
    50                  55                  60

His Pro Ser Leu Thr Cys Val Met Glu Gly Lys Asp Ile Glu Asp Trp
```

```
                65                  70                  75                  80
Ser Cys Cys Pro Thr Pro Trp Thr Ser Phe Gln Ser Ser Cys Tyr Phe
                85                  90                  95

Ile Ser Thr Gly Met Gln Ser Trp Thr Lys Ser Gln Lys Asn Cys Ser
                100                 105                 110

Val Met Gly Ala Asp Leu Val Val Ile Asn Thr Arg Glu Glu Gln Asp
                115                 120                 125

Phe Ile Ile Gln Asn Leu Lys Arg Asn Ser Ser Tyr Phe Leu Gly Leu
                130                 135                 140

Ser Asp Pro Gly Gly Arg Arg His Trp Gln Trp Val Asp Gln Thr Pro
145                 150                 155                 160

Tyr Asn Glu Asn Val Thr Phe Trp His Ser Gly Glu Pro Asn Asn Leu
                165                 170                 175

Asp Glu Arg Cys Ala Ile Ile Asn Phe Arg Ser Ser Glu Glu Trp Gly
                180                 185                 190

Trp Asn Asp Ile His Cys His Val Pro Gln Lys Ser Ile Cys Lys Met
                195                 200                 205

Lys Lys Ile Tyr Ile
210

<210> SEQ ID NO 16
<211> LENGTH: 261
<212> TYPE: DNA
<213> ORGANISM: Homo sapiens

<400> SEQUENCE: 16
atgattccag cagtggtctt gctcttactc cttttggttg aacaagcagc ggccctggga      60
gagcctcagc tctgctatat cctggatgcc atcctgtttc tgtatggaat tgtcctcacc     120
ctcctctact gtcgactgaa gatccaagtg cgaaaggcag ctataaccag ctatgagaaa     180
tcagatggtg tttacacggg cctgagcacc aggaaccagg agacttacga gactctgaag     240
catgagaaac caccacagta g                                               261
```

UNITED STATES PATENT AND TRADEMARK OFFICE
CERTIFICATE OF CORRECTION

PATENT NO. : 11,046,770 B2
APPLICATION NO. : 16/384811
DATED : June 29, 2021
INVENTOR(S) : Nakao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Twenty-second Day of November, 2022

Katherine Kelly Vidal
*Director of the United States Patent and Trademark Office*